United States Patent [19]
Cunningham et al.

[11] Patent Number: 6,011,180
[45] Date of Patent: *Jan. 4, 2000

[54] ACID-STABLE BORATES FOR PHOTOPOLYMERIZATION

[76] Inventors: Allan Francis Cunningham, Route de Bel-Air 18, Marly, Switzerland; Martin Kunz, Baslerstrasse 13/5, 79588 Efringen-Kirchen, Germany; Hisatoshi Kura, 5-3-15-205, Obayashi, Takarazuka, Hyogo 665, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/754,707

[22] Filed: Nov. 21, 1996

[30] Foreign Application Priority Data

Nov. 24, 1995 [CH] Switzerland .............................. 3343/95

[51] Int. Cl.$^7$ ...................................................... C07F 5/02
[52] U.S. Cl. .......................... 568/6; 568/1; 568/2; 564/8; 549/213; 544/358
[58] Field of Search ............................. 568/1, 2, 6; 564/8; 549/213; 544/358

[56] References Cited

U.S. PATENT DOCUMENTS

| | | | |
|---|---|---|---|
| 4,772,530 | 9/1988 | Gottschalk et al. ..................... | 430/138 |
| 4,772,541 | 9/1988 | Gottschalk et al. ..................... | 430/339 |
| 4,954,414 | 9/1990 | Adair et al. ............................... | 430/138 |
| 5,055,372 | 10/1991 | Shanklin et al. ........................ | 430/138 |
| 5,151,520 | 9/1992 | Gottschalk et al. ..................... | 548/110 |
| 5,168,032 | 12/1992 | Okamoto et al. ........................ | 430/281 |
| 5,500,453 | 3/1996 | Toba ......................................... | 522/25 |

FOREIGN PATENT DOCUMENTS

| | | |
|---|---|---|
| 353030 | 1/1990 | European Pat. Off. . |
| 0368629 | 5/1990 | European Pat. Off. . |
| 379157 | 7/1990 | European Pat. Off. . |
| 0407228 | 1/1991 | European Pat. Off. . |
| 0555058 | 8/1993 | European Pat. Off. . |
| 0661598 | 7/1995 | European Pat. Off. . |
| 0690074 | 1/1996 | European Pat. Off. . |

OTHER PUBLICATIONS

CA126:39711 abs of EP738928, Oct. 1996.
CA:116:184374 abs of Inorg Chem, Subramanian, 31(8) pp. 1540–1542, 1992.
CA:95:118331 abs of Proc electrochem Soc, Newman, 81–4(Proc Symp Lthium Batteries) pp. 131–143, 1981.
March editor of Advanced Organic Chem text, pp. 238–245, 1968.
CA:73:40481 abs of DE 1815868 by Borden, Nov. 1969.
Hawley's Condensed Chemical Dictionary 12th ed. p. 990, 1993.
"Review of light sensitive tetraarylborates" Photographic Science and Engineering, vol. 16, No. 4, Jul. & Aug. 1972.
C. Gardner Swain and Elmer C. Lupton, Jr., Journal of the American Chemical Society; 90:16, Jul. 31, 1968, p. 4328–4337—Filed and Resonance Components of Substituent Effects.
W.F. Little, et al., vol. 86, p. 1376–1381—Chronopotentiometric Studies of Ferrocene Derivatives. I. Determination of Substituent Constants with Substituted Phenylferrocenes[1].

*Primary Examiner*—Gary Geist
*Assistant Examiner*—Jean F Vollano
*Attorney, Agent, or Firm*—Luther A. R. Hall; David R. Crichton

[57] ABSTRACT

Compounds of the formula I

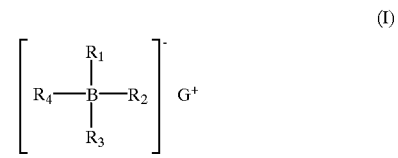

(I)

in which $R_1$ is, for example, $C_1$–$C_{20}$alkyl or phenyl-$C_1$–$C_6$alkyl which radicals are unsubstituted or substituted; $R_2$, $R_3$ and $R_4$ independently of one another are phenyl or biphenyl, which radicals are unsubstituted or substituted; wherein the sum of the Hammett σ constants ($\Sigma_\sigma$) of the substitutents on the aromatic radicals $R_2$, $R_3$ and $R_4$ is between +0.36 and +2.58; $R_8$, $R_9$, $R_{14}$, $R_{15}$ and $R_{16}$ are, for example, $C_1$–$C_{12}$alkyl, phenyl-$C_1$–$C_6$alkyl or phenyl, and G is a radical which is able to form positive ions. These compounds are suitable as photoinitiators for photopolymerizable compositions which contain acid groups, in the presence of a coinitiator if desired.

9 Claims, No Drawings

ACID-STABLE BORATES FOR PHOTOPOLYMERIZATION

The invention relates to highly reactive borate photoinitiator compounds which are stable in acid-containing media, to photopolymerizable compositions comprising these compounds, and to the use of the compounds as initiators for polymerization.

The use of borates as photoinitiators in combination with coinitiators is known in the prior art. For example, U.S. Pat. Nos. 4,772,530, 4,772,541 and 5,151,520 disclose triaryl alkyl borate anions with cationic dyes, for example cyanines, rhodamines, etc., as counterions. These compounds are employed as photoinitiators. In U.S. Pat. No. 4,954,414, cationic transition metal complexes are used together with triaryl alkyl borate anions in photopolymerizable compositions. From U.S. Pat. No. 5,055,372 it is also known to use quaternary ammonium compounds, for example tetramethylammonium, pyridinium, cetylpyridinium, etc., as cationic counterions to the triaryl alkyl borate. In this publication, the borates are employed in association with aromatic ketone initiator compounds as coinitiators in photocurable materials. These borates are unstable in media which contain components having acid groups, and can therefore not be employed as photoinitiators in such media.

For the extensive range of applications of photoinitiators, there is a requirement in the industry for stable reactive compounds, especially those which are stable in an acidic medium.

It has now surprisingly been found that certain monoborate compounds are sufficiently stable and reactive even in acid-containing media. The invention therefore provides compounds of the formula (I)

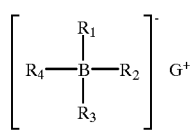
(I)

in which $R_1$ is $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl, where the radicals $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl can be interrupted by one or more groups O, $S(O)_p$ or $NR_5$, or where the radicals $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl are unsubstituted or are substituted by $C_1$–$C_{12}$alkyl, $OR_6$, $R_7S(O)_p$, $R_7S(O)_2O$, $NR_8R_9$, $SiR_{10}R_{11}R_{12}$, $BR_{13}R_{14}$ or $R_{15}R_{16}P(O)_q$;

$R_2$, $R_3$ and $R_4$ independently of one another are phenyl or biphenyl, where the radicals phenyl or biphenyl are unsubstituted or are substituted by unsubstituted or $OR_6$—, $NR_8R_9$— or halogen-substituted $C_1$–$C_{12}$alkyl, $OR_6$, $R_7S(O)_p$, $R_7S(O)_2O$, $R_8R_9NS(O)_2$, $NR_8R_9$, $NR_8R_9CO$,

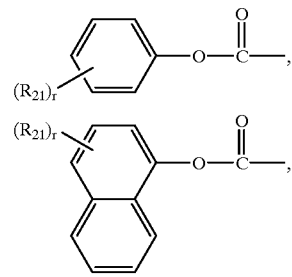

$SiR_{10}R_{11}R_{12}$, $BR_{13}R_{14}$, halogen, $R_{15}R_{16}P(O)_q$,

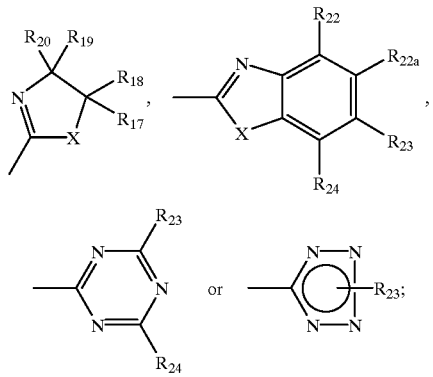

wherein the sum of the Hammett σ constants ($\Sigma_\sigma$) of the substitutents on the aromatic radicals $R_2$, $R_3$ and $R_4$ is between +0.36 and +2.58;

X is O, S or $NR_{21}$;

$R_5$ is hydrogen, $C_1$–$C_{12}$alkyl, phenyl-$C_1$–$C_6$alkyl which is unsubstituted or is substituted one to five times by $C_1$–$C_6$alkyl, $C_1$–$C_{12}$alkoxy or halogen, or phenyl which is unsubstituted or is substituted one to five times by $C_1$–$C_6$alkyl, $C_1$–$C_{12}$alkoxy or halogen;

$R_6$ and $R_7$ are unsubstituted or halogen-substituted $C_1$–$C_{12}$alkyl, phenyl- $C_1$–$C_6$alkyl which is unsubstituted or is substituted one to five times by $C_1$–$C_6$alkyl, $C_1$–$C_{12}$alkoxy or halogen, or phenyl which is unsubstituted or is substituted one to five times by $C_1$–$C_6$alkyl, $C_1$–$C_{12}$alkoxy or halogen;

$R_8$, $R_9$, $R_{10}$, $R_{11}$, $R_{12}$, $R_{13}$, $R_{14}$, $R_{15}$ and $R_{16}$ independently of one another $C_1$–$C_{12}$alkyl, $C_3$–$C_{12}$cycloalkyl, phenyl-$C_1$–$C_6$alkyl which is unsubstituted or is substituted one to five times by $C_1$–$C_6$alkyl, $C_1$–$C_{12}$alkoxy or halogen, or phenyl which is unsubstituted or is substituted one to five times by $C_1$–$C_6$alkyl, $C_1$–$C_{12}$alkoxy or halogen, or $R_8$ and $R_9$, together with the N atom to which they are attached, form a 6-membered aliphatic ring which as a further heteroatom may additionally contain oxygen or sulfur;

$R_{17}$, $R_{18}$, $R_{19}$ and $R_{20}$ independently of one another are hydrogen, unsubstituted or $C_1$–$C_{12}$alkoxy-substituted $C_1$–$C_{12}$alkyl, phenyl or phenyl-$C_1$–$C_6$alkyl, where the radicals phenyl or phenyl-$C_1$–$C_6$alkyl are unsubstituted or are substituted one to five times by $C_1$–$C_6$alkyl, $C_1$–$C_{12}$alkoxy or halogen;

p is a number from 0 to 2;

r is a number from 0 to 5;

$R_{21}$ is hydrogen or $C_1$–$C_{12}$alkyl;

$R_{22}$, $R_{22a}$, $R_{23}$ and $R_{24}$ independently of one another are hydrogen, unsubstituted or $C_1$–$C_{12}$alkoxy-, OH— or halogen-substituted $C_1$–$C_{12}$alkyl or unsubstituted or $C_1$–$C_{12}$alkoxy-, OH— or halogen-substituted phenyl;

q is 0 or 1; and

G is a radical which is able to form positive ions.

The invention likewise provides compositions comprising (a) at least one ethylenically unsaturated compound;

(b) at least one compound containing an acidic group, which acidic group may also be present in component (a);

(c) at least one photoinitiator of the formula (I); and (d) if desired, at least one coinitiator.

The compounds of the formula I are highly reactive initiators for the photopolymerization of ethylenically unsaturated compounds, with or without the addition of coinitiators.

In the compounds, the sum of the Hammettt σ constants ($\Sigma_o$) of the substitutents on the aromatic radicals $R_2$, $R_3$ and $R_4$ is between +0.36 and +2.58.

Substituted radicals phenyl or biphenyl are substituted from one to four times, for example once, twice or three times, especially once or twice.

$C_1$–$C_{20}$alkyl is linear or branched and is, for example, $C_1$–$C_{12}$, $C_1$–$C_8$, $C_1$–$C_6$ or $C_1$–$C_4$alkyl. Thus it is, for example, methyl, ethyl, propyl, isopropyl, n-butyl, sec-butyl, iso-butyl, tert-butyl, pentyl, hexyl, heptyl, 2,4,4-trimethyl-pentyl, 2-ethylhexyl, octyl, nonyl, decyl, undecyl, dodecyl, tetradecyl, pentadecyl, hexadecyl, heptadecyl, octadecyl, nonadecyl or eicosyl. For example, $R_1$ is $C_1$–$C_{12}$alkyl, especially $C_1$–$C_8$alkyl, preferably $C_1$–$C_6$alkyl, for example methyl or hexyl. Where $R_1$, $R_2$, $R_3$ and $R_4$ are $C_1$–$C_{20}$alkyl substituted by $R_9R_{10}R_{11}Si$, the alkyl radical is, for example, $C_1$–$C_{12}$alkyl, especially $C_1$–$C_8$alkyl, preferably $C_1$–$C_4$alkyl. Methyl is particularly preferred.

$C_1$–$C_{12}$alkyl and $C_1$–$C_6$alkyl are likewise linear or branched and have, for example, the definitions indicated above up to the corresponding number of C atoms. $R_5$, $R_6$, $R_7$, $R_8$, $R_9$, $R_{10}$, $R_{11}$, $R_{12}$ and $R_{13}$ are, for example, $C_1$–$C_8$alkyl, especially $C_1$–$C_6$alkyl, preferably $C_1$–$C_4$-alkyl, for example methyl or butyl. $C_1$–$C_6$alkyl substituents for phenyl-$C_1$–$C_6$alkyl, phenyl or biphenyl are, in particular, $C_1$–$C_4$alkyl, for example methyl or butyl. Cetyl is hexadecyl.

$C_2$–$C_{20}$alkyl interrupted one or more times by —O—, —S(O)$_p$— or —NR$_5$— is interrupted, for example, 1–9 times, for instance 1–7 times or once or twice, by —O—, —S(O)$_p$— oder —NR$_5$—. This produces, for example, structural units such as —CH$_2$—O—CH$_3$, —CH$_2$CH$_2$—O—CH$_2$CH$_3$, —[CH$_2$CH$_2$O]$_y$—CH$_3$, where y=1–9, —(CH$_2$CH$_2$O)$_7$CH$_2$CH$_3$, —CH$_2$—CH(CH$_3$)—O—CH$_2$—CH$_2$CH$_3$ or —CH$_2$—CH(CH$_3$)—O—CH$_2$—CH$_3$.

$C_3$–$C_{12}$cycloalkyl is, for example, cyclopropyl, cyclopentyl, cyclohexyl, cyclooctyl, cyclododecyl, especially cyclopentyl and cyclohexyl, preferably cyclohexyl.

$C_2$–$C_8$alkenyl radicals can be mono- or polyunsaturated and are, for example, allyl, methallyl, 1,1-dimethylallyl, 1-butenyl, 3-butenyl, 2-butenyl, 1,3-pentadienyl, 5-hexenyl or 7-octenyl, especially allyl. $R_4$ as $C_2$–$C_8$alkenyl is, for example, $C_2$–$C_6$alkenyl, especially $C_2C_4$alkenyl.

Phenyl-$C_1$–$C_6$alkyl is, for example, benzyl, phenylethyl, α-methylbenzyl, phenylpentyl, phenylhexyl or α,α-dimethylbenzyl, especially benzyl. Preference is given to phenyl-$C_1$–$C_4$-alkyl, especially phenyl-$C_1$–$C_2$alkyl. Substituted phenyl-$C_1$–$C_6$alkyl is substituted one to four times, for example once, twice or three times, especially once or twice, on the phenyl ring.

Substituted phenyl is substituted one to five times, for example once, twice or three times, especially once or twice, on the phenyl ring.

Naphthyl-$C_1$–$C_3$alkyl is, for example, naphthylmethyl, naphthylethyl, naphthylpropyl or naphthyl-1-methylethyl, especially naphthylmethyl. The alkyl unit can be either in position 1 or in position 2 of the naphthyl ring system. Substituted naphthyl-$C_1$–$C_3$alkyl is substituted once to four times, for example once, twice or three times, especially once or twice, on the aromatic rings.

$C_1$–$C_{12}$alkoxy denotes linear or branched radicals and is, for example, methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, isobutyloxy, tert-butyloxy, preferably methoxy.

Halogen is fluorine, chlorine, bromine and iodine, especially chlorine, bromine and fluorine, preferably chlorine and fluorine. Where $C_1$–$C_{20}$alkyl is substituted one or more times by halogen, there are, for example, 1 to 3 or 1 or 2 halogen substitutents on the alkyl radical.

Where $R_8$ and $R_9$, together with the N atom to which they are attached, form a ring, this ring is, for example, a piperidine ring. If the ring is interrupted by oxygen, the radical is, for example, morpholino.

Radicals which are generally suitable as counterion $G^+$ to the negative borate in the formula I are those which are able to form positive ions.

These are, for example, alkali metals, especially lithium or sodium, quaternary ammonium compounds, dye cations or cationic transition metal coordination complex compounds.

Preference is given to ammonium, tetraalkylammonium or dye cations. An example of tetraalkylammonium is tetra ($C_1$–$C_4$alkyl)ammonium. This refers to compounds of the following formula: $N(C_1$–$C_4alkyl)_4^+$, in which $C_1$–$C_4$alkyl can have the definitions indicated above up to the corresponding number of C atoms. Examples of appropriate ammonium compounds are tetramethylammonium, tetraethylammonium, tetrapropylammonium and tetrabutylammonium, especially tetramethylammonium and tetrabutylammonium. Benzyltri($C_1$–$C_4$alkyl)ammonium is also suitable. This is $C_6H_5$—CH$_2$—N($C_1$–$C_4$alkyl)$_3^+$, where $C_1$–$C_4$alkyl can have the definitions indicated above up to the corresponding number of C atoms. Examples of such radicals are benzyltrimethylammonium, benzyltriethylammonium, benzyltripropylammonium and benzyltributylammonium, especially benzyltrimethylammonium and benyzltributylammonium. However, trisalkylammonium ions are also suitable, for example trimethylammonium. Phosphonium and ammonium counterions of the formulae $^+PR_wR_xR_yR_z$ and $^+NR_wR_xR_yR_z$ are suitable, where $R_w$, $R_x$, $R_y$ and $R_z$ independently of one another are hydrogen, unsubstituted or substituted alkyl, cycloalkyl, alkenyl, phenyl or arylalkyl. Examples of substitutents of these alkyl, cycloalkyl, alkenyl, phenyl and aralkyl radicals are halides, hydroxyl, heterocycloalkyl (e.g. epoxy, aziridyl, oxetanyl, furanyl, pyrrolidinyl, pyrrolyl, thiophenyl, tetrahydrofuranyl, etc.), dialkylamino, amino, carboxyl, alkyl- and arylcarbonyl and aryloxy- and alkoxycarbonyl.

The tetravalent nitrogen may also be part of a 5- or 6-membered ring, which may in turn be fused onto other ring systems. These systems may also include additional heteroatoms, for example S, N, O.

The tetravalent nitrogen may also be part of a polycyclic ring system, for example azoniapropellane. These systems may also contain further heteroatoms, for example S, N, O.

Also suitable are polyammonium salts and polyphosphonium salts, especially the bis salts, in which it is possible for the same substitutents to be present as described above for the "mono" compounds.

The ammonium salts and phosphonium salts may also be substituted by neutral dyes (e.g. thioxanthenenes, thioxanthones, coumarins, ketocoumarins, etc.). Such salts are obtained by the reaction of the ammonium salts and phosphonium salts, substituted by reactive groups (e.g. epoxy, amino, hydroxyl, etc.), with appropriate derivatives of neutral dyes. Corresponding examples are described in EP-A 224 967 (Quantacure QTX).

Similarly, ammonium salts and phosphonium salts can also be substituted by colourless electron acceptors (e.g. benzophenones); examples of these are Quantacure ABQ

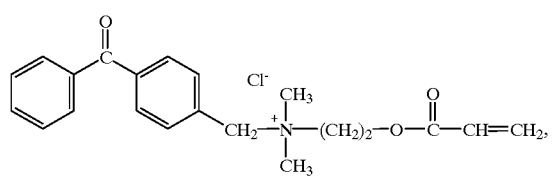

Quantacure BPQ

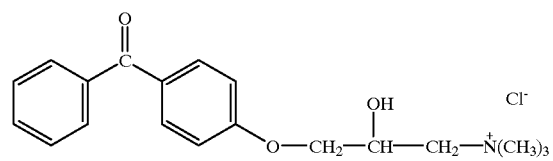

and Quantacure BTC

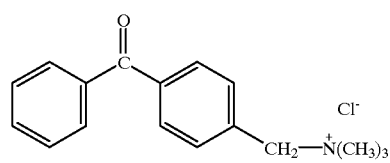

from International Bio-Synthetics.

Other quaternary ammonium compounds which are of interest are, for example, trimethylcetylammonium or cetylpyridinium compounds.

Other examples of positive counterions $G^+$ to be used in the compound of the formula I include the following:

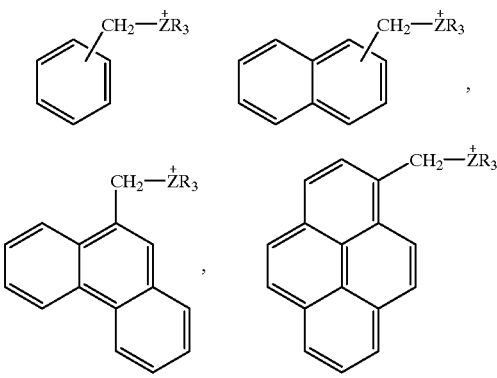

in which Z is P, S or N and R is an alkyl or aryl radical. Also suitable are compounds such as

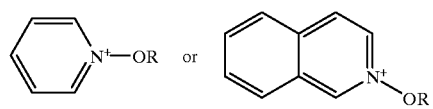

(described by Yagci et al. in J. Polym. Sci. Part A: Polymer Chem. 1992, 30, 1987 and Polymer 1993, 34(6), 1130), or compounds such as

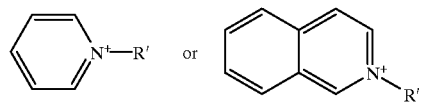

where R'=unsubstituted or substituted benzyl or phenacyl (described in JP-A Hei 7 70221). In these compounds, the aromatic rings in the pyridinium may also be substituted.

Other positive counterions $G^+$ to the borate which can be employed are further onium ions, for example iodonium or sulfonium ions.

Examples of such counterions to the borate are radicals of the formula

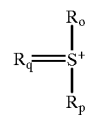

as described, for example, in EP-A 555 058 and EP-A 690 074. Also of interest as counterions are

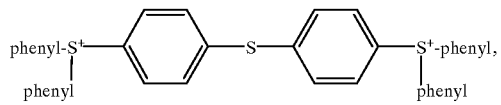

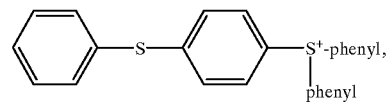

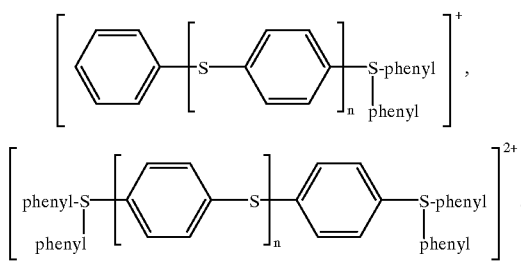

Further suitable counterions for the novel borates are cations of the formula

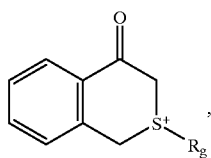

in which $R_g$ is an alkyl radical, especially ethyl, or is benzyl, and where the aromatic ring can carry further substituents.

Other suitable counterions are halonium ions, especially diaryliodonium ions, as described for example in EP-A 334 056 and EP-A 562 897.

However, cations of ferrocenium salts are also suitable, as described, for example, in EP-A-94915 and EP-A 109 851, for example

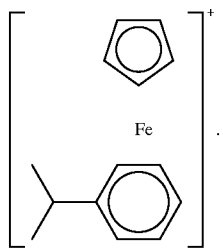

Other suitable onium cations, such as ammonium, phosphonium, sulfonium, iodonium, selonium, arsonium, tellonium and bismuthonium, are described, for example, in Japanese Patent Application Hei 6 266102.

Examples of cationic transition metal complex compounds which are suitable as counterions are described in U.S. Pat. No. 4,954,414. Of particular advantage are bis(2,2'-bipyridine)(4,4'-dimethyl-2,2'-bipyridine)ruthenium, tris(4,4'-dimethyl-2,2'-bipyridine)ruthenium, tris(4,4'-dimethyl-2,2'-bipyridine)iron, tris(2,2',2"-terpyridine)ruthenium, tris(2,2'-bipyridine)ruthenium and bis(2,2'-bipyridine)(5-chloro-1,10-phenanthroline)ruthenium.

Examples of dyes which are suitable as counterion are cations of triarylmethanes, for example malachite green, indolines, thiazines, for example methylene blue, xanthones, thioxanthones, oxazines, acridines, cyanines, rhodamines, phenazines, for example safranin.

Also suitable are dyes containing acid groups, for example methyl red, ethyl orange, methyl orange, acid yellow, rosolic acid, phenol red, fluorescein, Rose Bengal, thymolphthalein monophosphoric acid, auramine O, cresyl violet, rhodamine B, brilliant green or variamine blue.

If the compounds of the formula I do not contain a dye as counterion and at the same time the corresponding borate is not sufficiently absorptive, then it is expedient for the photopolymerization process to add at least one coinitiator or electron acceptor compound, (d) to the composition. In this application the term coinitiator refers for example also to sensitizers (=energy transfer compounds), for example thioxanthones, or dyes, reaction accelerators, for example amines, thiols, etc., preferably dyes. Examples of suitable dyes which can be added as coinitiators are described in U.S. Pat. No. 5,151,520. They are, for example, triarylmethanes, for example malachite green, indolines, thiazines, for example methylene blue, xanthones, thioxanthones, oxazines, acridines or phenazines, for example safranin.

As coinitiator it is also possible to use the above-described transition metal complex compounds or onium ion compounds.

Cationic, neutral or anionic dyes can be used as coinitiators for the novel compounds. Particularly suitable cationic dyes are malachite green, methylene blue, safranin O, rhodamines of the formula III

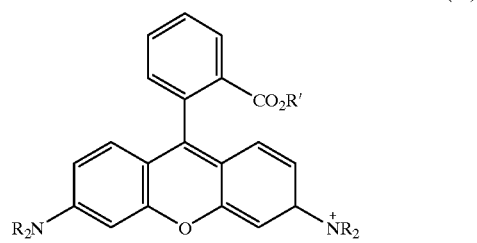

in which R and R' are alkyl or aryl radicals, for example rhodamine B, rhodamine 6G or violamine R, and also sulforhodamine B or sulforhodamine G.

Other suitable dyes are fluorones, as described for example by Neckers et al. in J. Polym. Sci., Part A, Poly. Chem, 1995, 33, 1691–1703.

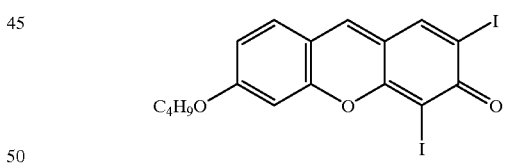

is particularly advantageous.

Examples of further suitable dyes are cyanines of the formula IV

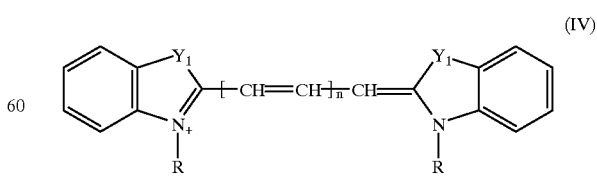

in which R=alkyl; n=0,1,2,3 or 4 and $Y_1$=CH=CH, N-CH$_3$, C(CH$_3$)$_2$, O, S or Se. Preferred cyanines are those in which $Y_1$ in formula IV is C(CH$_3$)$_2$ or S.

The following dye compounds are also suitable as coinitiators:

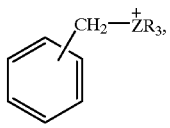

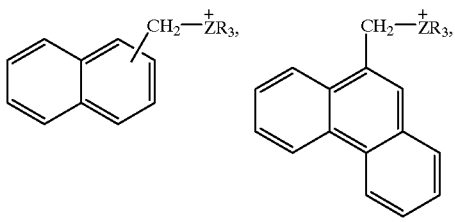

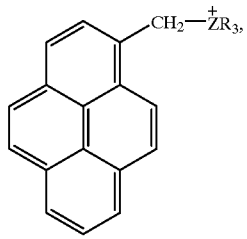

in which Z is P, S or N and R is an alkyl or aryl radical. Preferred compounds of the above formula are those in which $ZR_3$ is $N(CH_3)_3$, $N(C_2H_5)_3$ or $P(C_6H_5)_3$. Also suitable are compounds such

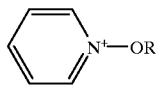

or

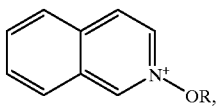

as described for example by Yagci et al. in J. Polym. Sci. Part A: Polymer Chem. 1992, 30, 1987 and Polymer 1993, 34(6), 1130, or, for example,

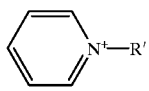

or

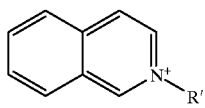

where R'=unsubstituted or substituted benzyl or phenacyl, described in JP-A Hei 7 70221. In these compounds rings in the pyridinium may also be substituted.

Other suitable dyes can be found, for example, in U.S. Pat. No. 4,902,604. These are azulene dyes. Of particular advantage as coinitiators for the novel compounds are the compounds 1–18 listed in columns 10 and 11 of this patent, in the Table.

Examples of further suitable dyes are merocyanine dyes, as described in U.S. Pat. No. 4,950,581 from column 6, line 20 to column 9, line 57.

As coinitiators for the novel compounds and photoinitiators it is also possible to use coumarin compounds. Examples of these are given in U.S. Pat. No. 4,950,581 in column 11, line 20 to column 12, line 42.

Other suitable coinitiators are xanthones or thioxanthones as described, for example, in U.S. Pat. No. 4,950,581, column 12, line 44 to column 13, line 15.

Anionic dye compounds can also be employed as coinitiators, for example. For instance, Rose Bengal, eosine or fluorescein are also suitable as coinitiators. Other suitable dyes, for example from the triarylmethane class or azo class, are described in U.S. Pat. No. 5,143,818.

Examples which are likewise suitable are benzoxanthene, benzothioxanthene, pyronine or porphyrin dyes or UV absorbers. These are, for example, thioxanthone derivatives, coumarins, benzophenone, benzophenone derivatives or hexaarylbisimidazole derivatives. Examples of suitable hexaarylbisimidazole derivatives are described in U.S. Pat. Nos. 3,784,557, 4,252,887, 4,311,783, 4,459,349, 4,410,621 and 4,622,286. 2-o-Chlorophenyl-substituted derivatives are particularly advantageous, for example 2,2'-bis(o-chlorophenyl)-4,4',5,5'-tetraphenyl-1,1'-bisimidazole. Other UV absorbers suitable in this context are, for example, polycyclic aromatic hydrocarbons, for example anthracene or pyrene, and also the triazines described in EP-A-137 452, in DE-A-27 18 254 and in DE-A-22 43 621. Other suitable triazines can be found in U.S. Pat. No. 4,950,581, column 14, line 60 to column 18, line 44. There is particular interest in trihalomethyltriazines, for example 2,4-bis(trichloromethyl)-6-(4-styrylphenyl)-s-triazine.

The sum of the Hammett σ constants ($\Sigma_\sigma$) of the substituents on the aromatic radicals $R_2$, $R_3$ and $R_4$ of the photoinitiators of the formula I in the novel compositions must lie between +0.36 and +2.58. This means that values which are greater than +0.36 and at the same time less than +2.58 must be present. Compounds having the values +0.36 and +2.58 are inactive in substrates containing acid-forming groups.

The sum of the a constants of the novel compounds is between +0.36 and +2.58, for example 0.39 and +2.52, +0.42 and +2.49, or +0.48 and +2.43, for example +0.54 +2.37 or +0.60 and +2.31, in particular between +0.69 and +2.04. σ constants were proposed by Hammett in order to quantify the effect of a substituent X on the dissociation of the corresponding benzoic acid $XC_6H_4COOH$. The a constants are defined by the following equation: $\log k/k_0 = \sigma\rho$, where $k_0$ is the equilibrium constant for $XC_6H_4COOH$, with X=H (that means benzoic acid), k is the constant for $XC_6H_4COOH$, and ρ is a reaction-specific constant for a reaction under defined conditions. Evidently, ρ has the value 1 for the dissociation of benzoic acid.

Hydrogen is assigned the σ constant 0.00, while electron donor groups, which hinder the dissociation of a substituted benzoic acid, receive negative σ constants. Electron-attracting groups, which increase the acidic strength of the substituted benzoic acid, have positive σ constants. The magnitude of the σ constants is dependent on field effects and resonance effects of the respective susbtituent. On this subject, compare J. March, Advanced Organic Chemistry, Third Edition, McGraw-Hill Book Company, New York, 1985, page 242–250. The Hammett equation is valid for a large number of reactions under widely varying reaction conditions (Jaffé, Chem. Rev. 1953, 53, 191–261). Little et al. determined (J. Amer. Chem. Soc, 1964, 86, 1376), for example, the Hammett a constants of substituents on phenylferrocenes. Factors which influence the oxidation of such ferrocene derivatives also play a role in the consideration of borate photoinitiators, since the production of initiating radicals takes place by oxidation of the borate. Little et al. also show a good correlation between the measured oxidation potentials of the ferrocene derivatives and the σ constants for meta and para substituents ($\sigma_m$, $\sigma_p$) from tabular values. Moreover, Little et al. produce a good connection between these values and the corresponding constants for ortho substituents ($\sigma_o$). In Can. J. Chem. Vol. 38,1960, 2493–2499, Charton states that the o and p values of the substituents are very similar. In the case where the tables published by Little and the tables listed below do not state values for o substituents, the corresponding values of the p substituents can be used. Values of $\sigma_o$, $\sigma_m$, and $\sigma_p$ for customary substituents can be taken, for example, from tables in the above-listed publications or are as given by C. Gardner Swain et al. in J. Amer. Chem. Soc. 1968 4328–4337. A detailed listing is also given by O. Exner in Correlation Analysis in Chemistry: Recent Advances, Plenum, New York, 1978, 439–540. For substituents not appearing in these lists, the values of the respective lay constants can be determined by measuring the oxidation potentials (as described by Little et al. in the articles cited above) or by determining the acidic strength of the corresponding benzoic acids.

Preference is given to compounds of the formula I in which $R_1$ is $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl, which radicals are unsubstituted or are substituted by $C_1$–$C_{12}$alkyl.

Also of interest are compounds of the formula I in which $R_1$ is $C_1$–$C_{12}$alkyl, allyl, cyclopentyl, cyclohexyl, benzyl or naphthylmethyl.

Preference goes, furthermore, to compounds of the formula I in which $R_2$, $R_3$ and $R_4$ independently of one another are phenyl or biphenyl, which radicals are unsubstituted or are substituted by unsubstituted or $OR_6$—, $NR_8R_9$— or fluorine-substituted $C_1$–$C_6$alkyl or by

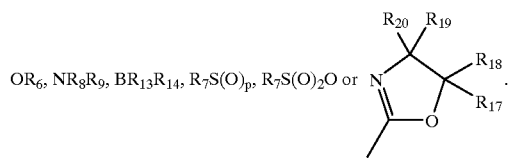

Further preferred compounds of the formula I are those in which $R_2$, $R_3$ and $R_4$ independently of one another are phenyl or biphenyl, which radicals are unsubstituted or are substituted by $C_1$–$C_{12}$alkyl, trifluoromethyl,

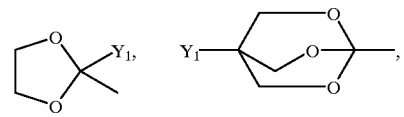

$OR_6$, $NR_8R_9$, halogen, $BR_{13}R_{14}$, $R_7S(O)_p$, $R_7S(O)_2O$ or

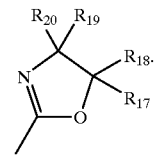

$Y_1$ is $C_1$–$C_{12}$alkyl or phenyl; $R_6$ is $C_1$–$C_{12}$alkyl, trifluoromethyl, or phenyl which is substituted by $C_1$–$C_6$alkyl, $C_1C_{12}$alkoxy or halogen; $R_7$ is $C_4$–$C_{12}$tert-alkyl, trifluoromethyl, or phenyl which is substituted by $C_1$–$C_6$alkyl, $C_1$–$C_{12}$alkoxy or halogen; $R_8$ and $R_9$ are $C_1$–$C_{12}$alkyl, phenyl or phenyl-$C_1$–$C_6$alkyl, or $R_8$ and $R_9$, together with the N atom to which they are attached, form a morpholino ring; $R_{13}$ and $R_{14}$ are phenyl which is substituted one to five times by $C_1$–$C_6$alkyl, $C_1$–$C_{12}$alkoxy or halogen; $R_{17}$, $R_{18}$, $R_{19}$ and $R_{20}$ independently of one another are phenyl which is unsubstituted or is substituted by $C_1$–$C_{12}$alkoxy-substituted $C_1$–$C_{12}$alkyl or by $C_1$–$C_6$alkyl, $C_1$–$C_{12}$alkoxy or halogen.

Other preferred compounds of the formula I are those in which $R_2$, $R_3$ and $R_4$ in the formula I are identical.

Compounds of the formula I which are also preferred are those in which G is a dye or metal complex cation, a sulfonium, sulfoxonium or iodonium cation, or G is a UV absorber compound which is able to form cations, or G is a metal cation of group I of the Periodic Table, or G is a cation $MY^+$ in which M is a metal from group II of the Periodic Table and Y is alkoxy or halogen, or G is an ammonium salt or phosphonium salt.

Preference is likewise given to compounds of the formula I in which $R_1$ is $C_1$–$C_6$alkyl, $R_2$, $R_3$ and $R_4$ are identical and are phenyl which is substituted by phenoxy, $R_8R_9NS(O)_2$,

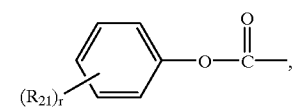

fluorine, bromine, chlorine, halogen-substituted $C_1$–$C_4$alkyl or

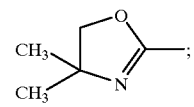

$R_8$ and $R_9$ are $C_1$–$C_4$alkyl; $R_{21}$ is $C_1$–$C_4$alkyl; r is the number 3; and G is ammonium, trimethylammonium, tetramethylammonium, tetrabutylammonium, tetradecylammonium, trimethyl-n-cetylammonium, cetylpyridinium, methyl-2-chloropyridinium, trimethylhydroxymethylammonium, triethyl-3-bromopropylammonium, triphenylsulfonium, diphenyliodonium, cyanine cation, methylene blue cation, safranin O cation, 3,4-dimethyl-2-(2-hydroxy-3-trimethylamino-propoxy)thioxanthone cation,

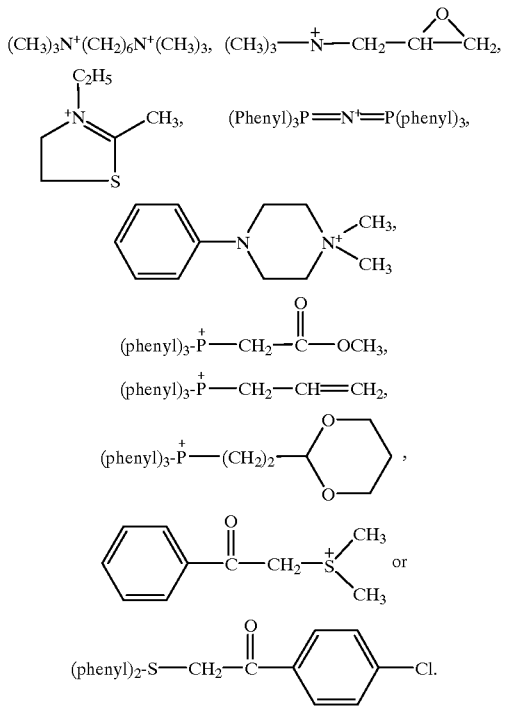

The compounds of the formula I can be obtained, for example, by reacting triorganoboranes (A) with organometallic reagents, for example alkyllithium compounds or Grignard reagents:

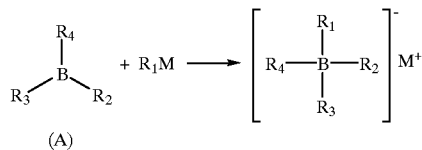

M is, for example, an alkali metal, such as Li or Na, or is MgX, where X is a halogen atom, especially Br.

Another option for preparing compounds of the formula I is, for example, the reaction of alkyldihaloboranes and/or alkyldi(alkoxy)boranes or alkyldi(aryloxy)boranes (B) with organometallic compounds, for example Grignard reagents or organolithium compounds:

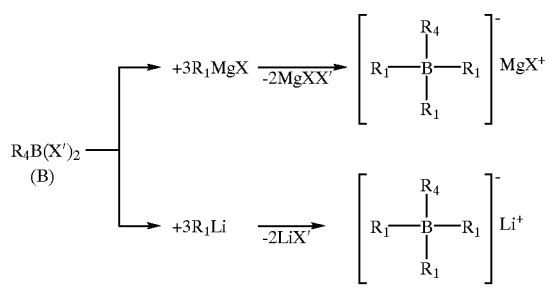

X is halogen, especially Br, X' is halogen, alkoxy or aryloxy. The definitions of the other radicals are as indicated above.

Where G in formula I above is a positive radical other than lithium or magnesium, these compounds can be obtained by cation exchange reactions, for example.

When working with organometallic reagents, the reaction conditions are generally familiar to the skilled worker. Thus the reaction is expediently carried out in an inert organic solvent, for example an ether or aliphatic hydrocarbon, such as diethyl ether, tetrahydrofuran or hexane.

Suitable organometallic reagents for preparing the novel polyborates are, for example, the lithium compounds of the corresponding aliphatic and aromatic hydrocarbons. The preparation of Grignard reagents, is known to the person skilled in the art and is described in many textbooks and other publications.

The reaction with the organometallic reagent is expediently carried out with the exclusion of air in an inert gas atmosphere, for example under nitrogen. The reaction is generally performed with cooling to 0° C. or below followed by heating to room temperature.

It is expedient to stir the reaction mixture. The products are isolated and purified by methods likewise generally known to the skilled worker, for example chromatography, recrystallization, etc.

Where the novel compounds of the formula I contain a dye radical as cation, they are prepared by the cation exchange reaction of an appropriate borate salt with a dye. Examples of the borate salts suitable for the exchange are the lithium, magnesium, sodium, ammonium or tetraalkylammonium salts.

Where the novel compounds of the formula I contain a transition metal complex as cation, they can be prepared by analogy with the method described in U.S. Pat. No. 4,954,414, column 7, section 2.

The preparation of some triorganoboranes (A) has been published, for example, by Wittig et al. in Chem. Ber. 1955, 88, 962.

The route towards some alkyldihaloboranes (B) has been set out, for example, by Brown et al. in JACS 1977, 99, 7097 and in U.S. Pat. No. 3,083,288. Mikailov et al. in Zh. Obshch. Khim. 1959, 29, 3405, and Tuchagues et al. in Bull. Chim. Soc. France, 1967, 11, 4160 also describe the preparation of such compounds. The alkyldialkoxyboranes and alkyldiaryloxyboranes can be prepared by various published procedures, for example those of Brown et al. Organometallics 1983, 2, 1316; Brown et al. Organometallics 1992, 11, 3094; Brown et al. J. Org. Chem. 1980, 2, 1316.

The boranes required as precursors for the novel compounds can be obtained, for example, in accordance with one of the published methods set out above.

In accordance with the invention the compounds of the formula I can be employed as photoinitiators for the photopolymerization of acidic compositions comprising at least one ethylenically unsaturated compound and at least one acidic group, which may also be present in the ethylenically unsaturated compound.

This use can also be implemented in combination with other photoinitiators, coinititators and/or other additives.

Examples of additives which may be used are coinitiators or electron acceptors, respectively. Examples of suitable coinitiators or electron acceptors are benzopteridenediones (described in JP Hei 02 113002), substituted benzophenones (for example Michler's ketone, Quantacure ABQ, Quantacure BPQ and Quantacure BTC from International Biosynthetics), trichloromethyltriazines (described in JP Hei 01 033548), metal complexes (described in JP Hei 04 261405), porphyrins (described in JP Hei 06 202548 and JP Hei 06 195014), coumarins and ketocoumarins (described in U.S. Pat. No. 4,950,581 and JP Hei 06 175557), p-aminophenyl compounds (described in EP-A 475153), xanthene (described in JP Hei 06 175566) and pyrrillium, thiopyrrillium and selenopyrrillium dyes (described in JP Hei 06 175563).

Other suitable additives are readily reducible compounds. The term readily reducible compound in this context includes compounds as described in U.S. Pat. No. 4,950,581, for example including iodonium salts, sulfonium salts, organic peroxides, compounds containing carbon-halide bonds (trichloromethyltriazines), heterocyclic sulfur compounds and other photoinitiators (α-amino ketones). Examples of other additives are heterocyles as described in the Patents and Patent Applications U.S. Pat. No. 5,168,032, JP 02 244050, JP 02 054268, JP 01 017048 and DE 383308.

Examples of further additives are aromatic imines, described in U.S. Pat. No. 5,079,126 and U.S. Pat. No. 5,200,292 (e.g. iminoquinone diazides), thiols, described in U.S. Pat. No. 4,937,159, thiols and N,N-dialkylanilines described in U.S. Pat. No. 4,874,685. It is also possible to employ two or more of the abovementioned electron acceptors and additives in combination.

As already mentioned, it is advantageous to combine the novel borate compounds with conitiators, inter alia, sensitizers (=energy transfer compounds). In this context, additionally and particularly, combinations with two or more different sensitizers, for example mixtures of the novel borate compounds with onium salts and thioxanthones or coumarins or dyes, are highly effective. Preferred onium salts in these mixtures are diphenyliodonium hexafluorophosphate, (p-octyloxyphenyl)(phenyl)iodonium hexafluorophosphate, or corresponding other anions of these compounds, for example the halides; and also sulfonium salts, for example triarylsulfonium salts (Cyracurel® UVI 6990, Cyracurel® UVI-6974 from Union Carbide; Degacure® KI 85 from Degussa or SP-150 und SP-170 from Asahi Denka). Preference is given, for example, to a mixture of the novel borate compounds with diphenyliodonium hexafluorophosphate and isopropylthioxanthone, to a mixture of the novel borate compounds with (p-octyloxyphenyl)(phenyl)iodonium hexafluorophosphate and isopropylthioxanthone, and to a mixture of the novel borate compounds with

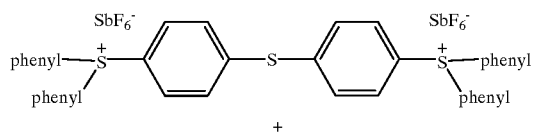

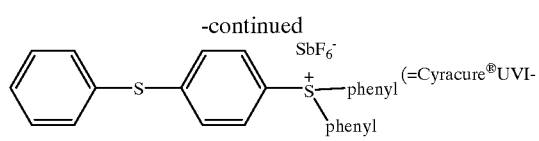

6974) and isopropylthioxanthone.

However, it is also particularly advantageous to add yet another photoinitiator, of the α-amino ketone type, to the abovementioned mixtures. For example, mixtures of the novel borates with onium salts and thioxanthones or dyes and α-amino ketones are highly effective. A preferred example is the mixture of the novel borate compounds with diphenyliodonium hexafluorophosphate or (p-octylphenyl)(phenyl)iodonium hexafluorophosphate, isopropylthioxanthone and (4-methylthiobenzoyl)methyl-1-morpholinoethane. A particularly suitable borate compound in these mixtures is tetramethylammonium hexyl-tris(m-fluorophenyl) borate.

The invention also provides a composition comprising, in addition to components (a), (b) and (c), at least one neutral, anionic or cationic dye or a thioxanthone and an onium compound. Also provided by the invention is such a composition additionally comprising a free-radical photoinitiator, especially an a-amino ketone compound.

Moreover, the invention provides a composition comprising in addition to components (a), (b) and (c) at least one compound of the formula XI

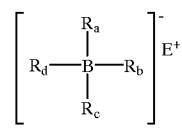

in which $R_a$, $R_b$, $R_c$ and $R_d$ independently of one another are $C_1$–$C_{12}$alkyl, trimethylsilylmethyl, phenyl, another aromatic hydrocarbon, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl or saturated or unsaturated heterocyclic radicals, wherein the radicals phenyl, another aromatic hydrocarbon, phenyl-$C_1$–$C_6$alkyl and saturated or unsaturated heterocyclic radical are unsubstituted or substituted by unsubstituted or $OR_6$—, $NR_8R_9$— or halogen-substituted $C_1$–$C_{12}$alkyl, $OR_6$, $R_7S(O)_p$, $R_7S(O)_2O$, $R_8R_9NS(O)_2$, $NR_8R_9$, $NR_8R_9CO$, $SiR_{10}R_{11}R_{12}$, $BR_{13}R_{14}$, halogen, $R_{15}R_{16}P(O)_q$;

$R_6$ and $R_7$ are unsubstituted or halogen-substituted $C_1$–$C_{12}$alkyl, phenyl-$C_1$–$C_6$alkyl which is unsubstituted or is substituted one to five times by $C_1$–$C_6$alkyl, $C_1$–$C_{12}$alkoxy or halogen, or phenyl which is unsubstituted or is substituted one to five times by $C_1$–$C_6$alkyl, $C_1$–$C_{12}$alkoxy or halogen;

$R_8$, $R_9$, $R_{10}$, $R_{11}$, $R_{12}$, $R_{13}$, $R_{14}$, $R_{15}$ and $R_{16}$ independently of one another are $C_1$–$C_{12}$alkyl, $C_3$–$C_{12}$cycloalkyl, phenyl-$C_1$–$C_6$alkyl which is unsubstituted or is substituted one to five times by $C_1$–$C_6$alkyl, $C_1$–$C_{12}$alkoxy or halogen, or phenyl which is unsubstituted or is substituted one to five times by $C_1$–$C_6$alkyl, $C_1$–$C_{12}$alkoxy or halogen, or $R_8$ and $R_9$, together with the N atom to which they are attached, form a 6-membered aliphatic ring which as a further heteroatom may additionally contain oxygen or sulfur;

p is a number from 0 to 2;

q is 0 or 1; and

E is a radical which is able to form positive ions, especially alkali metals, ammonium or tetraalkylammonium.

The definitions of the radicals $C_1$–$C_{12}$alkyl, trimethylsilylmethyl, phenyl, other aromatic hydrocarbons, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl, saturated or unsaturated heterocyclic radical and radical which is able to form positive ions, as well as for $R_6$–$R_6$, are as indicated above for formula I.

The invention additionally provides a composition comprising at least one borate of the formula I and at least one dye which changes or loses its colour during or after the. irradiation, which dye may also, as cation, be part of the compound of the formula I.

Examples of such dyes are cyanine dyes and pyrilium dyes.

The unsaturated compounds wihich are suitable as component (a) may include one or more olefinic double bonds. They may be of low (monomeric) or high (oligomeric) molecular mass. Examples of monomers containing a double bond are alkyl or hydroxyalkyl acrylates or methacrylates, such as methyl, ethyl, butyl, 2-ethylhexyl and 2-hydroxyethyl acrylate, isobornyl acrylate, methyl methacrylate and ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride and vinylidene chloride.

Examples of monomers containing two or more double bonds are the diacrylates of ethylene glycol, propylene glycol, neopentyl glycol, hexamethylene glycol and of bisphenol A, and 4,4'-bis(2-acryl-oyloxyethoxy) diphenylpropane, trimethyloupropane triacrylate, pentaerythritol toacrylate or tetraacrylate, vinyl acrylate, divinylbenzene, divinyl succinate, diallyl phthalate, triallyl phosphate, triallyl isocyanurate or tris(2-acryloyliethyl) isocyanurate.

Examples of polyunsaturated compounds of relatively high molecular mass (oligomers) are acrylisized epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is al so possible to employ vinyl ether monomers and oligomers, and also maleate-terminated otigomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the above-mentioned polyols, especially the aromatic polyols, and epichiorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris($\beta$-hydroxyethyl)amine, trimethylolethane, trimethylolapropane, pentaerythritol, dipentaerythritol and sorbitol.

The polyols may be partially or completely esterified with one or with diff erent unsaturated carboxylic acids, and in partial esters the free hydroxyl groups may be modified, for example etherified or esterified with other carboxylic acids.

Examples of esters are: trimethyloipropane triacrylate, trimethylolethane triacrylate, trimethylolpropane trimethacrylate, trimethylolethane trimethacrylate, tetram ethylene glycol dimethacrylate, triethylene glycol dimethacrylate, tetraethylene glycol diacrylate, pentaerythritol diacrylate, pentaeryth ritol triacrylate, pentaerythritol tetraacrylate, dipentaerythritol diacrylate, dipentaerythritol triacrylate, dipentaerythitol tetraacrylate, dipentaerythritol pentaacrylate, dipentaerythritol hexaacryl ate, tripentaerythritol octalscrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol dl,taconate, dipentaerythritol trisitaconate, dipentaerythritolpentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis(methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example, 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene, hexene, (meth)acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

The photopolymerizable compounds can be used alone or in any desired mixtures. It is preferred to use mixtures of polyol (meth)acrylates.

Compounds suitable as component (b) are those which are acids or carry an acidic group or are attached as ligand or counterion and which in the formulation adopt specific functions which are important to the ultimate properties.

These are all organic and inorganic Bronsted acids, for example carbonic acid, sulfuric acid, sulfonic acids, phosphorous acid, phosphoric acid, poly- and metaphosphoric acid, nitrous acid and nitric acid, acetic acid, oxalic acid, amino acids, etc., and also derivatives of these acids which retain their acidic character.

The compounds containing acidic groups are organic or inorganic molecules to which derivatives of the abovementioned Bronsted acids are attached.

These may be monomers, for example acrylic acid and methacrylic acid, maleic acid and fumaric acid; phthalic acid and its anhydrides, but also unsaturated fatty acids such as linolenic acid or oleic acid. Also relevant are oligomers and polymers containing acid groups, which may be either unsaturated or saturated and may either participate in the polymerization reaction or be used as film-forming binders. These polymers and oligomers can be monosubstituted, which is often achieved by termination using an acid-containing terminating reagent, or also polysubstituted, which is achieved by copolymerization of acid-modified monomers with unmodified monomers. Another possibility for introducing acid groups into an oligomer or polymer is the polymer-analogous reaction with acid-functionalized reagents. The acid-modified oligomers and polymers are, in particular, carboxylic and sulfonic acid-modified polyesters, polyacrylates, polyamides, polyurethanes, polyols, polyethers, polyepoxides, alkyd resins, polybutadienes, polyisoprenes, polystyrenes, polyimides, cellulose, cellulose esters, chlorinated polyolefins, polyvinylbutyral, polyallyl ethers, polyvinyl ethers, polycarbonates, polyacrylonitirile, polyisocyanates, melamine resins, and the copolymers formed from the monomer building blocks of the polymers listed.

Other compounds containing acid groups which are suitable as component (b) are dyes such as methyl red hydrochloride, ethyl orange, methyl orange, acid yellow, rosolic acid, phenol red, fluorescein, Rose Bengal, thymolphthalein monophosphoric acid, auramine O, cresyl violet, rhodamine B, brilliant green or variamine blue. Component (b) may likewise consist of pigments, fillers or other inorganic auxiliaries (for example filtration aids, antifoams, matting agents, wetting agents, agents for enhancing the scratch resistance or for improving the frictional properties, antisettling agents, emulsifiers, fungicides and biocides) which contain acid groups. Examples of pigments containing acid groups are sulfonated and phosphated phthalocyanines, diketopyrrolopyrroles, for example Irgazin DPP Red BL, indanthrones, for example Irgazin Blue A3RN and quinacridones, for example Chinquasia Red Y859. Examples of the fillers and auxiliaries include acidic silica gels, $BaSO_4$, $CaSO_4$, bleaching earths (for example Prolit, Tonsil Optimum), kieselguhr, silicic acid, kaolins, silica, bentonites, aluminium triphosphate, etc. Anticorrosion agents which contain acidic groups are also suitable as component (b), possible examples being phosphate and sulfates. Organic anticorrosion agents based on carboxylic acids are also employed, for example Irgacor 252. Other substances which fall under the definition of component (b) are those which alter the rheological properties of the formulation, including thickeners and flow aids. In most cases acidic organic polymers are employed as already described above, but branched and crosslinked polymers are also employed as thickeners. Spherical polymers, for example microgels, by contrast, enter the formulation as flow improvers. Modified fillers or pigments are likewise employed for this purpose, examples including aerosils and silicic acids.

Binders as well can be added to these novel compositions, and this is particularly expedient when the photopolymerizable compounds are liquid or viscous substances. The quantity of binder may, for example, be 5–95%, preferably 10–90% and especially 40–90% by weight relative to the overall solids content. The choice of binder is made depending on the field of application and on properties required for this yield, such as the capacity for development in aqueous and organic solvent systems, adhesion to substrates and sensitivity to oxygen.

Examples of suitable binders are polymers having a molecular weight of from about 5,000 to 2,000,000, preferably from 10,000 to 1,000,000. Examples are: homo- and copolymers of acrylates and methacrylates, for example copolymers of methyl methacrylate/ethyl acrylate/methacrylic acid, poly(alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene chloride copolymers, copolymers of vinylidene chloride with acrylonitrile, methyl methacrylate and vinyl acetate, polyvinyl acetate, copoly(ethylene-vinyl acetate), polymers such as polycaprolactam and poly(hexamethylenadipamide), and polyesters such as poly(ethylene glycol terephtalate) and poly(hexamethylene glycol succinate).

The unsaturated compounds can also be used as a mixture with non-photopolymerizable, film-forming components. These may, for example, be physically drying polymers or solutions thereof in organic solvents, for instance nitrocellulose or cellulose acetobutyrate.

They may also, however, be chemically and/or thermally curable (heat-curable) resins, examples being polyisocyanates, polyepoxides and melamine resins. The use of heat-curable resins at the same time is important for use in systems known as hybrid systems, which in a first stage are photopolymerized aof thermal aftertage are crosslinked by means of thermal aftertreatment.

Preference is given to compositions in which the coinitiator (d) is a dye or a UV absorber.

Particularly preferred compositions are those containing cyanine, merocyanine, anthraquinone, azo, diazo, acridine, coumarin, phenazine, phenoxazine, phenothiazine, rhodamine, xanthone, triphenylmethane or xanthene derivatives as dye.

Particular preference is given to cyanines of the formula I in which n=1–4, Y=C(CH$_3$)$_2$ or S and R=C$_1$–C$_{10}$alkyl.

Particularly preferred compositions are those in which the dye is cresyl violet, patent blue, brilliant blue, safranin O, fluorescein, rhodamine B, pyronine G4, azure A, lissamine green, ethyl orange or methylene blue.

Other preferred compositions are those in which the UV absorber is a thioxanthone derivative, a coumarin, benzophenone, a benzophenone derivative or a hexarylbisimidazole derivative.

In addition to the photoinitiator (c) the photopolymerizable mixtures may include various additives. Examples of these are thermal inhibitors, which are intended to prevent premature polymerization, examples being hydroquinone, hydroquinone derivatives, p-methoxyphenol, β-naphthol or sterically hindered phenols, such as 2,6-di-tert-butyl-p-cresol.

In order to increase the stability on storage in the dark it is possible, for example, to use copper compounds, such as copper naphthenate, stearate or octanoate, phosphorus compounds, for example triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface at the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenylbenzophenone, oxalamide or hydroxyphenyl-s-triazine type. These compounds can be used individually or in mixtures, with or without sterically hindered amines (HALS).

Examples of such UV absorbers and light stabilizers are
1. 2-(2'-hydroxlvphenyl)benzotriazoles for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)-benzotriazole, 2-(3',5'-di-tert-butyl-2-hydroxyphenyl)-5-chlorobenzotriazole, 2-(3'-tert-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2(3'-tert-butyl-5'-[2-(2-ethylhexyloxy)carbonylethyl]-2-hydroxyphenyl)benzotriazole, 2-(3-dodecyl-2'-hydroxy-5'-methylphenyl)benzotriazole, and 2-(3'-tert-butyl-2'-hydroxy- 5'-(2-isooctyloxycarbonylethyl) phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]benzotriazole with polyethylene glycol 300; [R-CH$_2$CH$_2$COO(CH$_2$)$_3$]$_2$- where R=3'-tert-butyl-4'-hydroxy-5'-2H-benzotriazol-2-yl-phenyl.
2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.
3. Esters of substituted or unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.
4. Acrylates, for example isooctyl or ethyl α-cyano-β,β-diphenyl acrylate, methyl α-carbomethoxycinnamate, butyl or methyl α-cyano-β-methyl-p-methoxycinnamate, methyl α-carbomethoxy-p-methoxycinnamate and N-(β-carbomethoxy-β-cyanovinyl)-2-methylindoline.

5. Sterically hindered amines, for example bis(2,2,6,6-tetramethylpiperidyl) sebacate, bis-(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethylene diamine and 4-tert-octylamino-2,6-dichloro-1,3,5-s-triazine, tris-(2,2,6,6-tetramethyl-4-piperidyl) nitrilotriacetate, tetrakis(2,2,6,6-tetramethyl-4-piperidyl)-1,2,3,4-butane tetraoate, 1,1'-(1,2-ethanediyl)bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro-[4.5]decane-2,4-dione, bis(1-octyloxy-2,2,6,6-tetramethylpiperidyl) sebacate, bis(1-octyloxy-2,2,6,6-tetramethylpiperidyl) succinate, condensation product of N,N'-bis(2,2,6,6-tetra-methyl-4-piperidyl) hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine und 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione and 3-dodecyl-1-(1,2,2,6,6-pentamethyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanalides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bi(2,4-dihydroxyphenyl)-1,3,5-triazine, 2(2,4-dihydroxyphenyl)-4,6-bis(2,4-dimethylphenyl)-1,3,5-triazine, 2,4-bis(2-hydroxy-4-propoxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1,3,5-triazine, 2-[4-dodecyl/tridecyl-oxy-(2-hydroxypropyl)oxy-2-hydroxy-phenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris(2,4-di-tert-butylphenyl) phosphite, diisodecyl pentaerythrityl diphosphite, bis(2,4-di-tert-butylphenyl) pentaerythrityl diphosphite, bis(2,6-di-tert-butyl-4-methylphenyl) pentaerythrityl diphosphite, bis-isodecyloxy pentaerythrityl diphosphite, bis(2,4-di-tert-butyl-6-methylphenyl) pentaerythrityl diphosphite, bis(2,4,6-tri-tert-butylphenyl) pentaerythrityl diphosphite, tristearyl sorbityl triphosphite, tetrakis(2,4-di-tert-butylphenyl)-4,4'-biphenylenediphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl) methylphosphite and bis(2,4-di-tert-butyl-6-methylphenyl)ethyl phosphite.

To accelerate the photopolymerization it is possible to add amines, for example triethanolamine, N-methyldiethanolamine, ethyl p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP-A-339 841. Other accelerators, coinitiators and autoxidizers are thiols, thioethers, disulfides or phosphines, as described in EP-A-438 123 and GB-A-2 180 358.

The photopolymerization can also be accelerized by adding further photosensitizers which shift or broaden the spectral sensitivity. These are, in particular, aromatic carbonyl compounds, for example benzophenone, thioxanthone, anthraquinone and 3-acylcoumarin derivatives and also 3-(aroylmethylene)thiazolines, but also eosine, rhodamine and erythrosine dyes.

The curing process can be assisted by, in particular, compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP-A-245 639.

Further customary additives, depending on the intended use, are fluorescent whiteners, fillers, pigments, dyes, wetting agents and levelling assistants. In order to cure thick and pigmented coatings it is appropriate to add glass microspheres or pulverized glass fibres, as described for example in U.S. Pat. No. 5,013,768.

The invention also provides compositions comprising as component (a) at least one ethylenically unsaturated photopolymerizable compound which is emulsified or dissolved in water.

Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are monoor polyfunctional, ethylenically unsaturated prepolymers which are known per se for aqueous prepolymer dispersions, can be initiated by free radicals and have, for example, a content of from 0.01 to 1.0 mol of polymerizable double bonds per 100 g of prepolymer and an average molecular weight of, for example, at least 400, in particular from 500 to 10,000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth)acrylates and of acrylic copolymers which contain α,β-ethylenically unsaturated acrylic radicals, as are described in EP-A-12 339. Mixtures of these prepolymers can likewise be used. Also suitable are the polymerizable prepolymers described in EP-A-33 896, which are thioether adducts of polymerizable prepolymers having an average molecular weight of at least 600, a carboxyl group content of from 02. to 15% and a content of from 0.01 to 0.8 mol of polymerizable C—C double bonds per 100 g of prepolymer. Other suitable aqueous dispersions, based on specific alkyl (meth)acrylate polymers, are described in EP-A-41 125, and suitable water-dispersible, radiation-curable prepolymers of urethane acrylates can be found in DE-A-29 36 039.

Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, matting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone and cellulose ethers. Emulsifiers which can be used are nonionic emulsifiers and, if desired, ionic emulsifiers as well.

The quantity of photoinitiator (b) in the photopolymerizable compositions is expediently from 0.05 to 15% by weight, preferably from 0.1 to 5% by weight, based on the composition.

In certain cases it may be of advantage to use mixures of two or more of the novel photoinitiators of the formula I. It is of course also possible to use mixtures with known photoinitiators, for example mixtures with benzophenone, acetophenone derivatives, for example α-hydroxycycloalkyl phenyl ketones, dialkoxyacetophenones, α-hydroxy- or α-aminoacetophenones, 4-aroyl-1,3-dioxolanes, benzoin alkyl ethers and benzil ketals, monoacyl phosphine oxides, bisacylphosphine oxides or titanocenes. Examples of particularly suitable additional photoinitiators are: 1-(4-dodecylbenzoyl)-1-hydroxy-1-methylethane, 1-(4-isopropylbenzoyl)-1-hydroxy-1-methylethane, 1-benzoyl-1-hydroxy-1-methylethane, 1-[4(2-hydroxyethoxy)-benzoyl]-1-hydroxy-1-methylethane, 1-[4(acryloyloxyethoxy) benzoyl]-1-hydroxy-1-methylethane, diphenyl ketone, penyl-1-hydroxycyclohexyl ketone, (4-morpholinobenzoyl)-1-benzyl-1-dimethylaminopropane, 1-(3,4-di-methoxyphenyl)-2-benzyl-2-dimethylamino-butan-1-one, (4-methylthiobenzoyl)-1-methyl-1-morpholinoethane, benzil dimethyl ketal, bis (cyclopentadienyl)bis(2,6-difluoro-3-pyrrylphenyl)titanium, cyclopentadienyl-arene-iron(II) complex salts, for example ($\eta^6$-iso-propylbenzene)($\eta^5$-cyclopentadienyl)iron(II) hexafluorophosphate, trimethylbenzoyldiphenylphosphine oxide, bis(2,6-dimethoxy-benzoyl)-(2,4,4-trimethylpentyl) phosphine oxide, bis(2,4,6-trimethylbenzoyl)-2,4-dipentoxyphenylphosphine oxide or bis(2,4,6-trimethylbenzoyl)phenylphosphine oxide. Other suitable additional photoinitiators can be found in U.S. Pat. No. 4,950,581 column 20, line 35 to column 21, line 35. Also suitable are triazine compounds, for example the triazines described in EP-A-137 452, in DE-A-27 18 254 and in DE-A-22 43 621. Further suitable triazines can be found in U.S. Pat. No. 4,950,581, column 14, line 60 to column 18, line 44. There is particular interest in trihalomethyltriazines, for example 2,4-bis(trichloromethyl)-6-(4-styrylphenyl)-s-triazine. Where the novel photoinitiators (c) are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17–25), aromatic sulfonium or iodonium salts (as described for example in U.S. Pat. No. 4,950,581, column 18, line 60 to column 19, line 10) or cyclopentadienyl arene iron(II) complex salts, for example ($\eta^6$-iso-propylbenzene)($\eta^5$-cyclopentadienyl)iron(II) hexafluorophosphate.

The invention therefore further provides compositions which in addition to the photoinitiator (c) also comprise at least one further photoinitiator (c') and/or other additives.

Compositions comprising as additional photoinitiator (c') a titanocene, a ferrocene, a benzophenone, a benzoin alkyl ether, a benzil ketal, a 4-aroyl-1,3-dioxolane, a dialkoxyacetophenone, an α-hydroxy- or α-aminoacetophenone, an α-hydroxycycloalkyl phenyl ketone, a xanthone, a thioxanthone, an anthraquinone or a mono- or bisacylphosphine oxide, or mixtures thereof, are of particular interest.

The photopolymerizable compositions can be used for various purposes, for example as printing ink, as a clear finish, as a white finish, for example for wood or metal, as a coating material, inter alia for paper, wood, metal or plastic, as a daylight-curable coating for roadmarking and the marking of buildings, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists or permanent resists, and as solder masks for electronic circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may if desired comprise glass fibres and other auxiliaries) and other thick-layered compositions, for coating or sealing electronic components, or as coatings for optical fibres.

The novel compounds may additionally be employed as initiators for emulsion polymerizations, as polymerization initiators for fixing ordered states of liquid-crystalline monomers and oligomers, or as initiators for fixing dyes on organic materials.

In coating materials, use Is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component (two-pack) systems together with a monounsaturated monomer, preferably with styrene. For photoresists, specific one-component systems are often used, for example polymaleimides, polychalcones or polyimides, as described in DE-A-2 308 830.

The novel compounds and mixtures thereof can also be used as free-radical photoinitiators or photoinitiating systems for radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings may also comprise binders as are described, for example, in DE-AlA 228 514 and in EP-A-636 669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE-A-4 228 514 and in EP-A-636 669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiators, the powder coating formulations may also include UV absorbers. Appropriate examples are listed above in sections 1–8.

The novel photocurable compositions are suitable, for example, as coating materials for substrates of all kinds, for example wood, textiles, paper, ceramics, glass, plastics such as polyfoters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, an image.

Coating of the substrates can be carried out by applying to the substrate a liquid composition, a solution or a suspension. The choice of solvent and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 $\mu$m to more than 100 $\mu$m.

The novel radiation-sensitive compositions find application as negative resists, having a very high sensitivity to light and being able to be developed in an aqueous alkaline medium. They are suitable as photoresists for electronics (electroplating resist, etch resist, solder resist), the production of printing plates, such as offset printing plates or screen printing plates, for use in chemical milling or as a microresist in the production of integrated circuits. The possible layer supports, and the processing conditions of the coating substrates, are just as varied.

The compounds according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recording include, for example, films of polyester, cellulose acetate or polymer-coated papers; substrates for offset printing plates are specially treated aluminium, substrates for producing printed circuits are copper-clad laminates, and substrates for producing integrated circuits are silicon wafers. The layer thicknesses for photographic materials and offset printing is generally from about 0.5 µm to 10 µm, while for printed circuits it is from 1 µm to about 100 µm.

Following the coating of the substrates, the solvent is removed, generally by drying, to leave a coat of the photoresist on the support.

The term "imagewise exposure" includes both exposure through a photomask comprising a predetermined pattern, for example a slide, exposure by means of a laser beam, which for example is moved under computer control over the surface of the coated substrate and in this way produces an image, and irradiation with computer-controlled electron beams.

Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes.

The photocurable composition may additionally be used in a process for producing printing plates or photoresists as is described, for example, in DE-A-40 13 358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printing inks, since the drying time of the binder is a critical factor for the production rate of graphic products, and should be in the order of fractions of seconds. UV-curable inks are particularly important for screen printing.

As already mentioned above, the novel mixtures are also highly suitable for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent.

Another field where photocuring is employed is the coating of metals, in the case, for example, of the coating of metal plates and tubes, cans or bottle caps, and photocuring of polymer coatings, for example of floor or wall coverings based on PVC.

Examples of the photocuring of paper coatings are the colourless varnishing of labels, record sleeves and book covers.

Also of interest is the use of the novel compounds for curing shaped articles made from composite compositions. The composite composition consists of a self-supporting matrix material, for example a glass fibre fabric, or alternatively, for example, plant fibres [cf. K. P. Mieck, T. Reussmann in Kunststoffe 85 (1995), 366–370], which is impregnated with the photocuring formulation. Shaped parts made of composite compositions, when produced using the novel compounds, attain a high level of mechanical stability and resistance. The novel compounds can also be employed as photocuring agents in moulding, impregnating and coating compositions as are described, for example, in EP-A-7086. Examples of such compositions are gel coat resins, which are subject to stringent requirements regarding curing activity and yellowing resistance, and fibre-reinforced mouldings, such as, for example, light diffusing panels which are planar or have lengthwise or crosswise corrugation. Techniques for producing such mouldings, such as hand lay-up, spray lay-up, centrifugal casting or filament winding, are described, for example, by P.H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing is carried out using medium-pressure mercury lamps as are conventional in UV curing. However, there is also particular interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of waveguide and optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated through a photomask with UV or visible light, and the unexposed areas of the layer are removed by treatment with a solvent (=developer). Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce printed electronic circuits and photoresists.

The photosensitivity of the novel compositions extends in general from about 200 nm through the UV region into the infrared region (about 20 000 µm, in particular 1200 µm) and therefore spans a very broad range. Suitable radiation is present, for example, in sunlight or light from artificial light sources. Consequently, a large number of very different types of light source are employed. Both point sources and arrays ("lamp carpets") are suitable. Examples are carbon arc lamps, xenon arc lamps, medium-, high- and low-pressure mercury lamps, possibly doped with metal halides (metal-halogen lamps), microwave-excited metal vapour lamps, excimer lamps, superactinic fluorescent tubes, fluorescent lamps, argon incandescent lamps, electronic flashlamps, photographic floodlamps, electron beams and X-rays, produced by means of synchrotrons or laser plasma. The distance between the lamp and the substrate to be exposed in accordance with the invention may vary depending on the intended application and the type and output of the lamp, and may be, for example, from 2 cm to 150 cm. Laser light sources, for example excimer lasers, such as krypton-F lasers for lighting at 248 nm, are especially suitable. Lasers in the visible region and in the IR region can also be employed. In this case, the high sensitivity of the novel materials is very advantageous. By this method it is possible to produce printed circuits in the electronics industry, lithographic offset printing plates or relief printing plates, and also photographic image-recording materials.

The invention therefore also provides a process for the photopolymerization of nonvolatile monomeric, oligomeric or polymeric compounds containing at least one ethylenically unsaturated double bond and at least one compound which comprises an acidic group, which acidic group may also be present in the ethylenically unsaturated compound, which comprises adding to the abovementioned compounds at least one compound of the formula I according to claim 1 in which G is a dye radical or a UV-absorber, or at least one compound of the formula I according to claim 1 in combination with at least one coinitiator, and irradiating the mixture with light from the infrared region through the UV region up to a wavelength of 200 nm, and the invention also provides for the use of a composition as described above for producing pigmented and nonpigmented coating materials, powder coatings, printing inks, printing plates, adhesives, dental compositions, waveguides, optical switches, colour proofing systems, glass fibre cable coatings, screen printing stencils, resist materials, for photographical reproduction processes, for encapsulating electrical and electronic components, for producing composite compositions, for producing magnetic recording materials, for producing three-dimensional objects by means of stereolithography, and as image-recording material, especially for holographic recordings.

The invention additionally provides a coated substrate which is coated on at least one surface with a composition as described above, and provides a process for the photographic production of relief images, in which a coated substrate is subjected to imagewise exposure and then the unexposed portions are removed with a solvent. Of particular advantage in this context is the laser beam exposure already mentioned above.

The novel compounds of the formula I are white powders which are stable in air. As already mentioned above, in the compounds the sum of the Hammett a constants ($\Sigma\sigma$) of the substituents on the aromatic radicals in $R_2$, $R_3$ and $R_4$ is between +0.36 and +2.58. These compounds are acid-stable and can be employed in acidic photopolymerizable formulations as photohardeners.

The novel borate compounds can be employed not only as initiators for photopolymerization reactions but also as thermal polymerization initiators. Consequently, the invention also provides for the use of the compounds of formula I as initiators for the thermal polymerization of compounds containing ethylenically unsaturated double bonds, and a process for the thermal polymerization of compounds containing ethylenically unsaturated double bonds, which comprises employing at least one compound of the formula I as polymerization initiator.

The examples which follow illustrate the invention in more detail. Parts and percentages are, as in the remainder of the description and in the claims, by weight, unless stated otherwise.

Where alkyl radicals having more than three C atoms are referred to without any mention of specific isomers, the n-isomers are meant in each case.

EXAMPLE 1

Method A: Procedure for Preparing Borates from Triorganylboranes

Tetramethylammonium butyl tris(2,6-difluorophenyl) borate 1.0 equivalent of butyllithium (0.012 mol) in hexane is added at 0° C. to a solution of 5.0 g (0.012 mol) of tris(2,6-difluorophenyl)borane in 20 ml of tetrahydrofuran (THF) at a rate such that the temperature does not exceed 5° C. The reaction mixture is allowed to warm to room temperature and is stirred for 0.5 h. The mixture is subsequently concentrated in vacuo and the oily residue is dissolved in 80 ml of a 4:1 mixture of methanol and water. Following filtration, and treatment of the filtrate with 3.95 g (0.036 mol) of tetramethylammonium chloride, a white solid precipitates. This precipitate is filtered off, washed with water and dried in vacuo, to give 3.3 g (57% of theory) of the borate, having a melting point of >230° C. The shift d in the $^{11}$B-NMR spectrum in $CD_3COCD_3$ is –13,21 ppm.

EXAMPLE 2

Method B: Procedure for the Preparation of Borates from Alkyidihaloboranes

Tetramethylammonium hexyl tris(p-chlorophenyl) borate A small portion of a solution of 5.8 g (0.03 mol) of 1-bromo-4-chlorobenzene in 30 ml of THF is added to a suspension of 0.73 g (0.03 mol) of magnesium turnings in 10 ml of THF. The reaction mixture is heated until the Grignard reaction begins. When the reaction begins, heating is discontinued and the rest of the 1-bromo-4-chlorobenzene solution is added dropwise over the course of 20 minutes so as to retain a gentle reflux. Following the addition, heating is resumed until the remaining magnesium has been consumed. In a different reaction vessel, 10 ml of THF are added slowly to 3.2 g (0.01 mol) of hexyldibromoborane dimethyl sulfide which has been cooled to 0° C. The Grignard solution is then added dropwise at the same temperature over the course of 30 minutes, and the mixture is refluxed for 2 hours once addition is complete. The mixture is subsequently evaporated in vacuo and the resulting oily residue is dissolved in 80 ml of 4:1 mixture of methanol and water. Following filtration and treatment of the filtrate with 3.3 g (0.03 mol) of tetramethylammonium chloride, a white solid precipitates. This precipitate is filtered off, washed with water and dried in vacuo, to give 2.8 g of the borate. Recrystallization from methanol gives 1.75 g (35% of theory) of pure borate with a melting point of 154–156° C. The shift d in the $^{11}$B-NMR spectrum in $CD_3COCD_3$ is −9.87 ppm.

EXAMPLE 3

Method C Preparation of Hexyl Tris(3-trifluoromethylphenyl) Borate 9.4 ml of a solution of butyllithium in hexane (1.6 M, 0.015 mol) is added at −78° C. to a solution of 3.38 g (0.015 mol) of 1-bromo-3-trifluoromethylbenzene in 15 ml of diethyl ether at a rate such that the temperature does not exceed −65° C. After stirring for 2.5 hours at −78° C., 0.74 g of difluorohexylborane is added over the course of 5 minutes and the reaction mixture is allowed to warm to room temperature. After one hour of stirring at room temperature, the reaction mixture is evaporated and dissolved in 20 ml of a 2:1 mixture of methanol and water. The solution is filtered and treated with 1.1 g (0.01 mol) of ammonium chloride. Following the addition of 50 ml of water, the methanov/water solution is subjected to extraction with ethyl acetate. The extracts are dried over $MgSO_4$, filtered and concentrated to give a yellow oil, which is purified by treatment with hot hexane to give 0.9 g (i.e. 30% of theory) of the title compound as a yellow oil. The shifts for the $^1$H-NMR spectrum are given in Table 1A. The sum of the s constants for the title compound is +1.29.

EXAMPLES 4–27

The borate compounds of Examples 4–27 are prepared in analogy to the Methods A, B or C described in Examples 1–3, using the corresponding boranes. The structures and physical data of the compounds are given in Table 1 below.

TABLE 1

$[(R_1)_3{-}B{-}R_2]^-X^+$

| Ex. | $R_2$ | $R_1$ | $X^+$ | Method | Melting point [° C.] | $d^{11}B$—NMR [ppm] | $\Sigma_\sigma$ |
|---|---|---|---|---|---|---|---|
| 1 | Butyl | 2,6-Difluorophenyl | $N(CH_3)_4$ | A | >230 | −13.21 | +0.72 |
| 2 | Hexyl | 4-Chlorophenyl | $N(CH_3)_4$ | B | 154–156 | −9.93 | +0.69 |
| 3 | Hexyl | 3-Trifluoromethylphenyl | $NH_4$ | C |  | **** | +1.29 |
| 4*[7] | Butyl | 3-Fluorophenyl | $N(CH_3)_4$ | B | 117–119 | −9.70 | +1.02 |
| 5 | Hexyl | 3-Fluorophenyl | $N(CH_3)_4$ | B | 113–120 | −4.94 | +1.02 |
| 5a | Ethyl | 3-Fluorophenyl | $N(CH_3)_4$ | A | 156–160 | *** | +1.02 |
| 5b | Ethyl | 3-Fluorophenyl | $N(C_4H_9)_4$ | A | 78–79 | *** | +1.02 |
| 6 | Hexyl | 3-Fluorophenyl | QTX*[1] | B | 63–65 |  | +1.02 |
| 7 | Hexyl | 3-Fluorophenyl | Cyanin*[2] | B | <20 |  | +1.02 |
| 8 | Hexyl | 3,5-Difluorophenyl | $N(CH_3)_4$ | B | 87–88 | −8.89 | +2.04 |
| 9 | Methyl | 2-(Trifluoromethyl)phenyl | $N(CH_3)_4$ | A | 219–220 | **** | +1.62 |
| 10 | Butyl | 2-(Trifluoromethyl)phenyl | $N(CH_3)_4$ | A | *** | **** | +1.62 |
| 11 | Butyl | 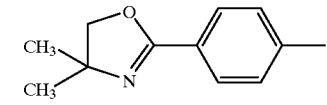 | $N(CH_3)_4$ | B | 220–222 | **** | +1.02++ |
| 12 | Methyl | 4-Bromophenyl | $N(CH_3)_4$ | A | * | ** | +0.69 |
| 13 | Hexyl | 3-Chlorophenyl | $N(CH_3)_4$ | B | 104–105 | −9.33 | +1.11 |
| 14 | Hexyl | 4-Bromophenyl | $N(CH_3)_4$ | B | 156–159 | −10.14 | +0.69 |

TABLE 1-continued $$[(R_1)_3—B—R_2]^- X^+$$

| Ex. | $R_2$ | $R_1$ | X$^+$ | Method | Melting point [° C.] | d$^{11}$B—NMR [ppm] | $\Sigma_\sigma$ |
|---|---|---|---|---|---|---|---|
| 15 | Butyl | 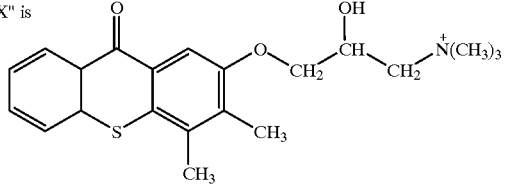 | N(CH$_3$)$_4$ | B | * | ** | +0.93$^{++}$ |
| 16 | Benzyl | m-Fluorophenyl | N(CH$_3$)$_4$ | A | 223–227 | −3.43 | +1.02 |
| 17 | Hexyl | m-Fluorophenyl | N(C$_4$H$_9$)$_4$ | B | 78–80 | −4.93 | +1.02 |
| 18 | Hexyl | m-Fluorophenyl | N(C$_{10}$H$_{21}$)$_4$ | B | <20 | −10.27 | +1.02 |
| 19 | Hexyl | m-Fluorophenyl | Iodonium*$^3$ | B*$^{3a}$ | <20 | −4.91 | +1.02 |
| 20 | Hexyl | m-Fluorophenyl | Pyrylium*$^4$ | B*$^{4a}$ | 80–82 | −4.92 | +1.02 |
| 21 | Hexyl | m-Fluorophenyl | Methylene blue cation | B*$^{5a}$ | 135–138 | **** | +1.02 |
| 22 | Hexyl | m-Fluorophenyl | Safranin O cation | B*$^{6a}$ |  | −4.93 | +1.02 |
| 23 | Hexyl | m-Phenoxyphenyl | N(CH$_3$)$_4$ | C | <20 | −4.80 | +0.75 |
| 24 | Hexyl | p-(Diisopropyl-aminosulfonyl)-phenyl | N(CH$_3$)$_4$ | C | >230 | −4.79 | +1.89 |
| 25 | Hexyl | p-(2,6-di-t-butyl-4-methylphenoxy-carbonyl)-phenyl | N(CH$_3$)$_4$ | C | 208–213 | −3.47 | +1.35 |
| 26 | Hexyl | p-(Diisopropyl-aminocarbonyl)-phenyl | N(CH$_3$)$_4$ | C | >230 | −4.93 | +1.05 |
| 27 | Methyl | Dichloromesityl | N(CH$_3$)$_4$ | A | 155–158 | −6.98 | +1.53 |

*$^1$ "QTX" is

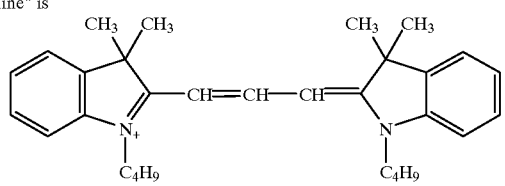

*$^2$ "Cyanine" is

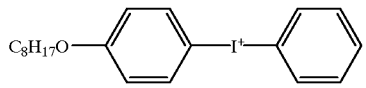

*$^3$ "Iodonium" is

*$^{3a}$(p-Octyloxyphenyl)(phenyl)iodonium tosylate

*$^4$ "Pyrylium" is

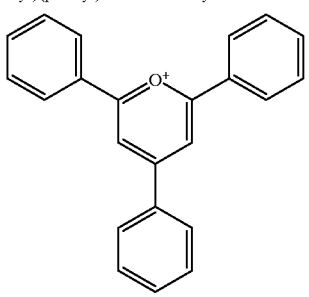

*$^{4a}$Prepared using 2,4,6-triphenylpyrylium chloride
*$^{5a}$Prepared using methylene blue (chloride)

TABLE 1-continued

[(R₁)₃—B—R₂]⁻X⁺

| Ex. | R₂ | R₁ | X⁺ | Method | Melting point [° C.] | d¹¹B—NMR [ppm] | Σσ |
|---|---|---|---|---|---|---|---|

*⁶ᵃPrepared using safranin O (chloride)
*⁷Compound 4 was also prepared, starting from butyldiisopropoxyborane and in accordance with Method B, in a yield of 47%
***Not determined
****The values for the ¹H—NMR spectrum measured in CD₃CN are given in Table 1A below.

⁺⁺ In calculating Σσ the value for 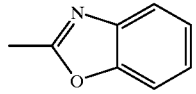 was used.

TABLE 1A

| Example | Shift d [ppm], coupling constant J [Hz] |
|---|---|
| 3 | 7.55 (br s,3); 7.51 (br s,3); 7.21 (br d,6,J = 5); 3.04 (s,12), 1.30–1.17 (m,6); 1.03–0.90 (m,4); 0.85 (t,3,J = 6.5) |
| 9 | 7.49 (dd,3,J = 7.2); 7.06–6.98 (m,6); 6.92 (br m,3); 3.03 (s,12); 0.47 (br m,3) |
| 10 | 7.45–7.38 (m,6); 7.12–7.01 (m,6); 3.02 (s,12); 1.27 (br m,2); 1.10–0.74 (br m,4); 0.76 (t,3,J = 7) |
| 11 | 7.84 (d,6,J = 9); 7.44 (d,6,J = 9); 3.99 (s,6); 3.39 (s,12); 1.24 (s,18); 1.24–1.10 (m,2); 0.88 (br m,4); 0.75 (t,3,J = 7) |
| 12 | 7.15–7.05 (br m,12); 3.29 (s,12); 0.24 (br m,3) |
| 13 | 7.27 (br s,6); 7.14 (t,3,J = 7.7);6.99 (d,3,J = 7.7); 3.13 (s,12), 1.51–1.29 (m,6); 1.12–0.93 (m,7) |
| 15 | 7.92 (br s,3); 7.55 (br d,3,J = 7.5); 7.45 (dt,3,J = 8,1.5); 7.14 (t,3,J = 7.5); 4.24 (s,6); 3.28 (s,12); 1.35 (s,18); 1.35–1.20 (m,2); 1.05–0.82 (m,4); 0.79 (t,3,J = 7.5) |
| 21 | 7.87 (d,2,J = 10); 7.33 (dd,2,J = 10,2); 7.18 (d,2,J = 2); 7.02–6.95 (m,6); 6.89 (br d,3,J = 11); 6.54 (brt,3,J = 9); 3.30 (s,12); 1.25–1.19 (m,6); 0.95–0.80 (m,7) |

EXAMPLES 28–46

The compounds of Examples 28–46 are prepared in analogy to Method B. For all compounds, Σσ is +1.02. The structure and physical data of the compounds is shown in Table 2.

TABLE 2

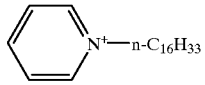 = anion

| Example | Cation | Melting point [° C.] | d$^{11}$B—NMR [ppm] |
|---|---|---|---|
| 28 | $^+$N(CH$_3$)$_3$(n-C$_{16}$H$_{33}$) | ++ | −10.24 (CDCl$_3$) |
| 29 | 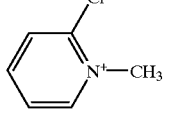 | ++ | −10.18 (CDCl$_3$) |
| 30 | 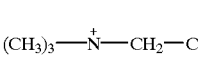 | 80–81 | −4.94 (Acetone-d$_6$) |
| 31 | $^+$N(CH$_3$)$_3$(CH$_2$OH) | ++ | −4.94 (Acetone-d$_6$) |
| 32 | (CH$_3$)$_3$N$^+$(CH$_2$)$_6$N$^+$(CH$_3$)$_3$ | ++ | −4.95 (Acetone-d$_6$) |
| 33 | $^+$N(C$_2$H$_5$)$_3$([CH$_2$]$_3$Br) | ++ | −4.95 (Acetone-d$_6$) |
| 34 | 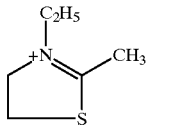 | ++ | −4.95 (Acetone-d$_6$) |
| 35 | 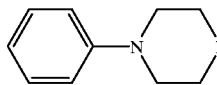 | ++ | −4.94 (Acetone-d$_6$) |
| 36 | (Phenyl)$_3$P=N$^+$=P(Phenyl)$_3$ | 130–135 | −4.94 (Acetone-d$_6$) |
| 37 | 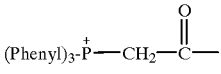 | ++ | −4.94 (Acetone-d$_6$) |
| 38 | (CH$_3$)$_3$N$^+$H | ++ | −4.94 (Acetone-d$_6$) |
| 39 | 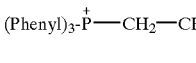 | ++ | −4.93 (Acetone-d$_6$) |
| 40 | (Phenyl)$_3$-$\overset{+}{P}$—CH$_2$—CH=CH$_2$ | ++ | −4.91 (Acetone-d$_6$) |
| 41 | 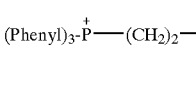 | ++ | −4.92 (Acetone-d$_6$) |
| 42 | (Phenyl)$_3$S$^+$ | 48–50 | −4.94 (Acetone-d$_6$) |
| 43 | 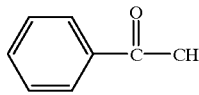 | ++ | −4.94 (Acetone-d$_6$) |

TABLE 2-continued

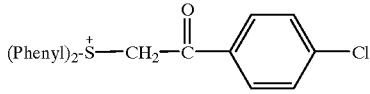

| Example | Cation | Melting point [° C.] | $d^{11}B$—NMR [ppm] |
|---|---|---|---|
| 44 | (Phenyl)-I⁺-(Phenyl) | 92–95 | −4.93 (Acetone-$d_6$) |
| 45 | (Phenyl)$_2$-S⁺—CH$_2$—C(=O)—C$_6$H$_4$—Cl | ++ | −4.90 (Acetone-$d_6$) |

++ melting point not determined, because the substance is an oil or resin

EXAMPLE 46

Photocuring of an acrylate mixture A photocurable composition is prepared from

| | |
|---|---|
| 45.1 g | of ® Scripset 540 (styrene-maleic anhydride copolymer, Monsanto) |
| 48.3 g | of trimethylolpropane triacrylate |
| 6.6 g | of polyethylene glycol diacrylate |
| 150.0 g | of acetone | and in each case 0.4% of the respective photoinitiator compound and 0.3% of Quantacure QTX (corresponding to the formula given above, with chloride as counterion) are added.

The mixture is stirred at room temperature for 1–2 hours in order to dissolve the photoinitiator. All operations are carried out under red light. The samples to which initiator has been added are applied to 300 μm aluminium foil (10×15 cm). The solvent is removed by drying at room temperature for 5 minutes and then heating at 60° C. in a convection oven for 15 minutes. Over the liquid film there is placed a 76 μm thick polyester film, on which is laid a standardized test negative with 21 steps of different optical density (Stouffer wedge).

A second polyester film is applied over this assembly, and the resulting laminate is fixed on a metal plate. The sample is then exposed for 40 seconds using a 4 kW xenon lamp at a distance of 30 cm. Following exposure the cover films and the mask are removed, and the exposed film is developed with 0.85% strength aqueous sodium carbonate solution in an ultrasound bath and then dried at 40° C. in a convection oven for 5 minutes. The sensitivity of the initiator system used is characterized by indicating the last wedge step reproduced without tack. The higher the number of steps, the more sensitive the system. On this scale, an increase by two steps denotes approximately a doubling of the curing rate. The results are reproduced in Tables 2a–2c.

TABLE 2a

| Borate from Example | Number of steps cured |
|---|---|
| 1 | 9 |
| 2 | 7 |
| 14 | 6 |
| 4 | 11 |
| 5 | 11 |
| 8 | 8 |
| 9 | 9 |
| 11 | 6 |

TABLE 2b

| Borate from Example | Number of steps cured |
|---|---|
| 13 | 10 |
| 27 | 7 |

TABLE 2c

| Borate from Example | Number of steps cured |
|---|---|
| 17 | 7 |
| 23 | 7 |
| 26 | 12 |

EXAMPLE 47

The procedure of Example 46 is repeated but using 0.3% of the compound from Example 6, containing the QTX radical as cation, instead of a mixture of 0.4% of borate compound and 0.3% of Quantacure QTX. The number of steps cured is 10.

EXAMPLE 48

The procedure of Example 46 is repeated but using 0.3% of the compound from Example 7, containing a cyanine radical as cation, instead of a mixture of 0.4% of borate compound and 0.3% of Quantacure QTX. The number of steps cured is 12.

EXAMPLE 49
The procedure of Example 46 is repeated but using 0.4% of the compound from Example 5 and 0.3% of a dye instead of a mixture of 0.4% of borate compound and 0.3% of Quantacure QTX. The dyes used and results obtained are listed in Tables 3 to 3c.
TABLE 3
| Dye | Number of steps reproduced | Bleaching behaviour* |
|---|---|---|
| 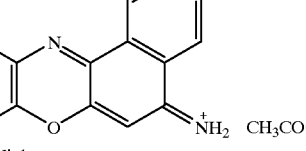 Cresyl Violet | 15 | b |
| 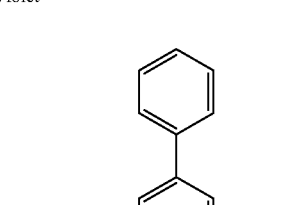 | 16 | b |
| 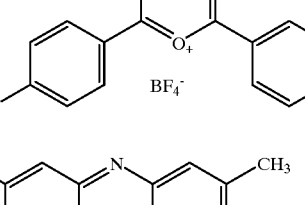 Safranin O | 16 | — |
| 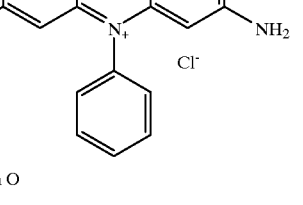 Brilliant Green | 12 | — |
| 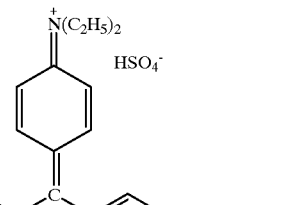 Methylene Blue | 12 | b |

TABLE 3-continued
| Dye | Number of steps reproduced | Bleaching behaviour* |
|---|---|---|
| 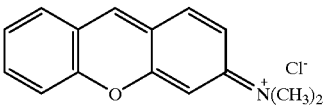<br>Pyronine GY | 15 | — |
| 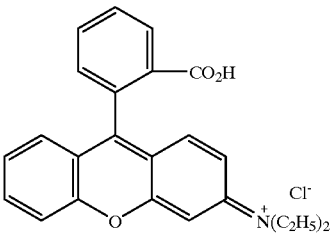<br>Rhodamine B | 17 | — |
TABLE 3a
| Dye | Number of steps reproduced | Bleaching behaviour* |
|---|---|---|
| 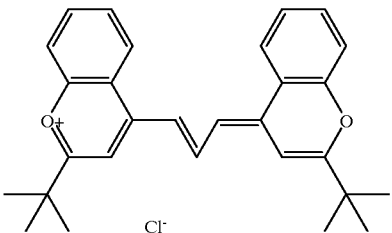 | 15 | b |
| 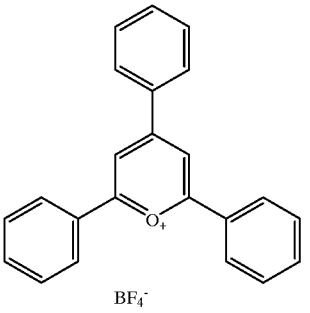 | 17 | b |
*b = Bleaches out (visual examination)
— = No bleaching is observed; however, this does not mean that it does not occur, but only that it is not noted in the course of visual examination TABLE 3b
| Dye | Number of steps reproduced | Bleaching behaviour* |
|---|---|---|
| 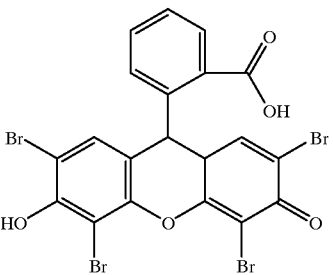 Eosine | 14 | b |
| 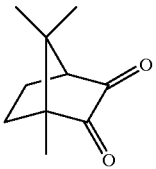 Camphorquinone | 6 | — |
| 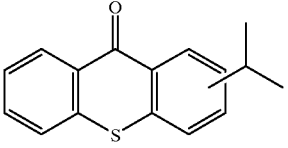 Quantacure ITX | 5 | — |
| 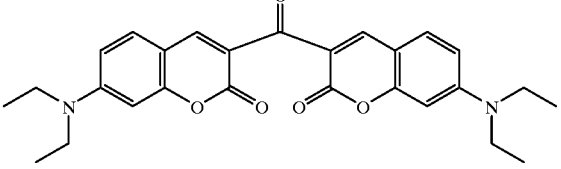 | 12 | — |
| 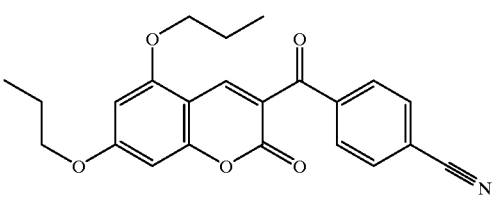 | 12 | — |
| 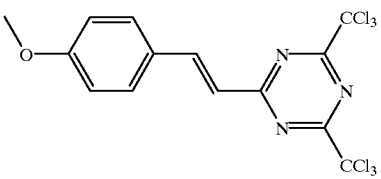 | 12 | — |

TABLE 3b-continued

| Dye | Number of steps reproduced | Bleaching behaviour* |
|---|---|---|
| [structure: carbazole with N-butyl, bearing two -C(=O)-C(CH$_3$)(N-morpholino)(CH$_2$-CH=CH$_2$) groups] | 12 | — |

*b = Bleaches out (visual examination)
— = No bleaching is observed; however, this does not mean that it does not occur, but only that it is not noted in the course of visual examination

TABLE 3c

| Dye | Number of steps reproduced |
|---|---|
| [structure: o-Chloro-hexaarylbisimidazole dimer] o-Chloro-hexaarylbisimidazole | 7 |

EXAMPLE 50

Reactivity test in a solder resist A photocurable composition is prepared by mixing the following components:

| | |
|---|---|
| 37.64 g | of trimethylolpropane trisacrylate |
| 10.76 g | of ® Cymel 301, hexamethoxymethylmelamine (American Cyanamid, USA) |
| 47.30 g | of ® Carboset 525, thermoplastic polyacrylate containing carboxyl groups (B. F. Goodrich) |
| 4.30 g | of polyvinylpyrrolidone PVP (GAF, USA) |
| 319.00 g | of methylene chloride and |
| 30.00 g | of methanol. |

Portions of this composition are mixed with in each case 0.8% of the compound from Example 5 and 0.6% of a dye, based on the solids content. All operations are carried out under red light. The samples to which initiator has been added are applied in a dry-film thickness of 35 µm to a 200 mm aluminium foil (10×15 cm). The solvent is removed by heating at 60° C. in a convection oven for 15 minutes. Onto the liquid film there is placed a 76 µm thick polyester film, over which a standardized test negative with 21 steps of different optical density (Stouffer wedge) is applied. The sample is covered with a second UV-transparent film and is pressed on a metal plate by means of vacuum. The sample is then exposed for 40 seconds using a MO61/5 kW lamp at a distance of 30 cm. Following exposure, the cover films and the mask are removed and the exposed film is developed with 0.85% strength aqueous sodium carbonate solution in an ultrasound bath for 240 seconds and is then dried at 60° C. in a convection oven for 15 minutes. The sensitivity of the initiator system used is characterized by indicating the last wedge step reproduced without tack. The higher the number of steps, the more sensitive the system. The results are given in Tables 4 and 4a.

TABLE 4

| Dye | Number of steps reproduced | Bleaching behavior* |
|---|---|---|
| Cresyl Violet | 10 | — |
| Safranin O | 15 | — |
| Brilliant Green | 10 | — |
| Rhodamine B | 17 | — |
| Pyronine GY | 15 | b |
| Methylene blue | 15 | b |

*b = Bleaches out (visual examination)
— = No bleaching is observed; however, this does not mean that it does not occur, but only that it is not noted in the course of visual examination

TABLE 4A

| Dye | Number of steps reproduced | Bleaching behaviour* |
|---|---|---|
| 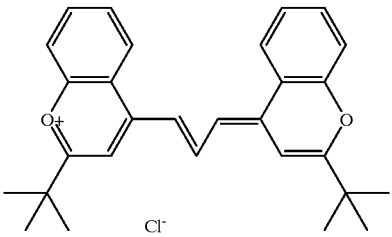 | 12 | b |
| 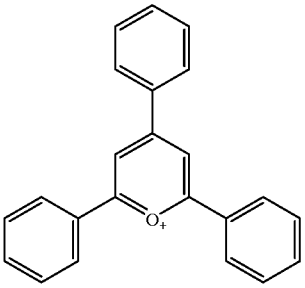 | 16 | b |

*b = Bleaches out (visual examination)
— = No bleaching is observed; however, this does not mean that it does not occur, but only that it is not noted in the course of visual examination

EXAMPLE 51

A photocurable composition is prepared by mixing the following components:

- 37.64 g of trimethylolpropane trisacrylate
- 10.76 g of ® Cymel 301, hexamethoxymethylmelamine (American Cyanamid, USA)
- 47.30 g of ® Carboset 525, thermoplastic polyacrylate containing carboxyl groups (B. F. Goodrich)
- 4.30 g of polyvinylpyrrolidone PVP (GAF, USA)
- 319.00 g of methylene chloride and
- 30.00 g of methanol.

Portions of this composition are mixed with 0.6% of the compound from Example 5, and 0.4% of isopropylthioxanthone, 0.8% of diphenyliodonium hexafluorophosphate, based on the solids content. All operations are carried out under red light. The samples to which initiator has been added are applied in a dry-film thickness of 35 µm to a 200 mm aluminium foil (10×15 cm). The solvent is removed by heating at 60° C. in a convection oven for 15 minutes. Onto the liquid film there is placed a 76 µm thick polyester film, over which a standardized test negative with 21 steps of different optical density (Stouffer wedge) is applied. The sample is covered with a second UV-transparent film and is pressed on a metal plate by means of vacuum. The sample is then exposed for 10, 20 or 40 seconds using an SMX-3000 metal halide-doped high-pressure mercury lamp at a distance of 30 cm. Following exposure, the cover films and the mask are removed and the exposed film is developed with 1% strength aqueous sodium carbonate solution in an ultrasound bath for 180 seconds at 30° C. and is then dried at 60° C. in a convection oven for 15 minutes. The sensitivity of the initiator system used is characterized by indicating the last wedge step reproduced without tack. The higher the number of steps, the more sensitive the system. The results are given in Table 5.

TABLE 5

| Number of steps reproduced after | | |
|---|---|---|
| 10 s | 20 s | 40 s |
| 8 | 10 | 12 |

EXAMPLE 52

A photocurable composition is prepared by mixing the following components:

- 37.64 g of trimethylolpropane trisacrylate
- 10.76 g of ® Cymel 301, hexamethoxymethylmelamine (American Cyanamid, USA)
- 47.30 g of ® Carboset 525, thermoplastic polyacrylate containing carboxyl groups (B. F. Goodrich)
- 4.30 g of polyvinylpyrrolidone PVP (GAF, USA)
- 319.00 g of methylene chloride and
- 30.00 g of methanol.

Portions of this composition are mixed with 0.6% of the compound from Example 5, 0.4% of isopropylthioxanthone, 0.8% of diphenyliodonium hexafluorophosphate and 0.4% of (4-methylthiobenzoyl)-methyl-1-morpholinoethane, based on the solids content. Sample preparation and exposure are as described in Example 33. The results are presented in Table 6.

TABLE 6

| Number of steps reproduced after | | |
|---|---|---|
| 10 s | 20 s | 40 s |
| 10 | 12 | 14 |

EXAMPLE 53

A photocurable composition is prepared by mixing the following components:

- 37.64 g of trimethylolpropane trisacrylate
- 10.76 g of ®Cymel 301, hexamethoxymethylmelamine (American Cyanamid, USA)
- 47.30 g of ®Carboset 525, thermoplastic polyacrylate containing carboxyl groups (B.F.Goodrich)
- 4.30 g of polyvinylpyrrolidone PVP (GAF, USA)
- 319.00 g of methylene chloride and
- 30.00 g of methanol.

Portions of this composition are mixed with 0.4% of the compound from Example 5, 0.4%

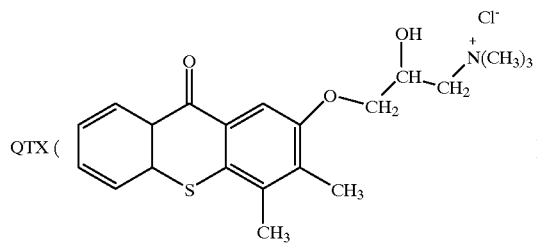

and 0.4% of (4-methylthiobenzoyl)methyl-1-morpholinoethane, based on the solids content. Sample preparation and exposure are as described in Example 33. The results are presented in Table 7.

TABLE 7

| Number of steps reproduced after | | |
|---|---|---|
| 10 s | 20 s | 40 s |
| 9 | 11 | 13 |

EXAMPLE 54

The procedure of Example 46 is repeated but using 0.4% of the compound from Example 20, containing the 2,3,6-triphenylpyrylium as cation, instead of a mixture of 0.4% of borate compound and 0.3% of Quantacure QTX. The number of steps cured is 13. Bleaching out of the film was observed.

EXAMPLE 55

The procedure of Example 46 is repeated but using 0.4% of the compound from Example 21, containing the methylene blue as cation, instead of a mixture of 0.4% of borate compound and 0.3% of Quantacure QTX. The number of steps cured is 15. Bleaching out of the film was observed.

EXAMPLE 56

The procedure of Example 46 is repeated but using 0.4% of the compound from Example 22 containing the safranin O as cation, instead of a mixture of 0.4% of borate compound and 0.3% of Quantacure QTX. The number of steps cured is 17. Bleaching out of the film was observed.

EXAMPLE 57

The procedure of Example 46 is repeated but using a mixture of 0.4% of borate compound and 0.3% of safranin O. The results are reproduced in Table 8.

TABLE 8

| Borate from Example | Number of steps cured |
|---|---|
| 28 | 13 |
| 30 | 12 |
| 31 | 16 |
| 34 | 15 |
| 35 | 16 |
| 36 | 15 |
| 37 | 12 |
| 38 | 16 |
| 39 | 14 |
| 40 | 15 |
| 41 | 15 |
| 42 | 13 |
| 43 | 14 |
| 44 | 15 |
| 45 | 15 |

*b = Bleaches out (visual examination)
— = No bleaching is observed; however, this does not mean that it does not occur, but only that it is not noted in the course of visual examination

EXAMPLE 58

The procedure of Example 46 is repeated but using a mixture of 0.4% of the compound from Example 5 and 0.3% of dye. In addition, the xenon lamp is replaced by a frequency-doubled Nd/YAG laser (COHERENT DPSS 532-50, beam diameter 0.7 mm, divergence <1.3 mrad) with monochromatic light of wavelength 532 nm and with an output of 50 mW. The laser beam, with a diameter of about 3.3 mm, is moved at a rate of 6 mm/s over a 21-step Stouffer wedge fixed to the sample. Development leaves a line varying in width and length. For evaluation, a statement is made of the number of steps at which a cured line can still be seen. The dyes used and results obtained are listed in Table 9.

TABLE 9

| Dye | Number of steps reproduced | Bleaching behaviour* |
|---|---|---|
| Cyanine | 4 | — |
| Safranin O | 13 | — |

TABLE 9-continued

| Dye | Number of steps reproduced | Bleaching behaviour* |
|---|---|---|
| Rhodamine B | 12 | — |
| Pyronine GY | 12 | b |
| Methylene blue | 7 | b |
| Cresyl Violet | 10 | |
| [structure 8: 2,6-diphenyl-4-(4-methoxyphenyl)pyrylium BF$_4^-$ — but with phenyl at 4 and methoxyphenyl at 2] | 8 | |
| [structure 9: bis(2-tert-butyl-chromenylium) methine dye, Cl$^-$] | 9 | b |
| [structure: 2,4,6-triphenylpyrylium BF$_4^-$] | 9 | b |

*b = Bleaches out (visual examination)
— = No bleaching is observed; however, this does not mean that it does not occur, but only that it is not noted in the course of visual examination

EXAMPLE 59

A photocurable formulation is prepared by mixing the following components:

- 10.0 g of dipentaerythritol monohydoxypenta acrylate, ®SR 399, Sartomer Co., Berkshire, GB
- 15.0 g of tripropylene glycol diacrylate, Sartomer Co., Berkshire, GB
- 15.0 g of N-vinylpyrrolidone, Fluka
- 10.0 g of trimethylolpropane triacrylate, Degussa
- 50.0 g of urethane acrylate ®Actylan AJ20, Société Nationale des Poudres et Explosifs
- 0.3 g of levelling assistant ®Byk 300, Byk-Mallinckrodt Portions of this composition are mixed with 0.4%, based on the total quantity of the formulation, of the compound 5 and 0.3% of a dye. All operations are carried out under red light. The formulations are applied to a 300 μm aluminium foil. The thickness of the dry film is 60 μm. To this film there is applied a 76 mm thick polyester film. Exposure is carried out using a frequency-doubled NdlNYAG laser (COHERENT DPSS 532-50, beam diameter 0.7 mm, divergance <1.3 mrad) with monochromatic light of wavelength 532 nm and with an output of 50 mW. The laser beam, with a diameter of about 3.3 mm, is moved at a rate of 6 mm/s over a 21-step Stouffer wedge fixed to the sample. Following exposure, the cover films and the mask are removed and the exposed film is developed in ethanol in an ultrasound bath at 23° C. for 10 seconds. Drying is carried out at 40° C. in a convection oven for 5 minutes. Development leaves a line varying in width and length. For evaluation, a statement is made of the number of steps at which a cured line can still be seen. The dyes used and results obtained are given in Table 10:

TABLE 10

| Dye | Number of steps reproduced | Bleaching behaviour* |
|---|---|---|
| Safranin O | 11 | — |
| Rhodamine B | 13 | — |
| Pyronine GY | 9 | b |
| Methylene blue | 10 | b |
| [2,4,6-triphenylpyrylium BF$_4^-$] | 7 | b |

EXAMPLE 60

The same formulations as in Example 57 are used, and portions of this composition are mixed with 0.4%, based on the total quantity of the formulation, of the compound 5 and 0.3% of a dye. All operations are carried out under red light. The samples are placed in pill bottles with a diameter of about 3 cm. These formulations, in the bottles, are exposed using a frequency-doubled Nd/YAG laser (COHERENT DPSS 532-50, beam diameter 0.7 mm, divergence <1.3 mrad) with monochromatic light of wavelength 532 nm and with an output of 50 mW for 10 seconds at a distance of 30 cm. Following exposure, the uncured formulation is poured out and the remaining, cured layer is developed in ethanol in an ultrasound bath at 23° C. for 10 seconds. Drying takes place at 40° C. in a convection oven for 5 minutes. After development, there remains a needle-like figure which varies in length. For evaluation, the length of the figure is stated, which is a measure of the capacity for through-curing. The dyes used and results obtained are reproduced in Table 11:

TABLE 11

| Dye | Length of the figure formed, in mm |
|---|---|
| Safranin O | 3 |
| Rhodamine B | 2 |
| Pyronine GY | 8 |
| Methylene blue | 8 |

TABLE 11-continued

| Dye | Length of the figure formed, in mm |
|---|---|
| [2,4,6-triphenylpyrylium BF$_4^-$] | 8 |

EXAMPLE 61

The procedure of Example 50 is repeated but using 0.4% of the dye-borate salts. Moreover, the xenon lamp is replaced by a frequency-doubled Nd/YAG laser (COHERENT DPSS 532-100, beam diameter 0.7 mm, divergence <1.3 mrad) with monochromatic light of wavelength 532 nm and with an output of 100 mW. The laser beam, with a diameter of about 3.3 mm, is moved at a rate of 6 mm/s over a 21-step Stouffer wedge fixed to the sample. Development leaves a line varying in width and length. For evaluation, a statement is made of the number of steps at which a cured line can still be seen. The dyes used and results obtained are listed in Table 12.

TABLE 12

| Compound | Number of steps reproduced |
|---|---|
| 21 | 9 |
| 22 | 12 |

EXAMPLE 62

The procedure of Example 60 is repeated but using dye-borate salts in concentrations such that the optical density of a 2 mm film for the wavelength 532 nm is 0.5, and compound 5 is additionally used. Deviating from Example 61, use is made of a frequency-doubled Nd/YAG laser (COHERENT DPSS 532-100, beam diameter 0.7 mm, divergence <1.3 mrad) with monochromatic light of wavelength 532 nm and with an output of 100 mW, and exposure is carried out for 5 seconds at a distance of 30 cm. The results are presneted in Table 13.

TABLE 13

| Compound | Concentration of compound 5 | Length of the figure formed, in mm |
|---|---|---|
| 0.05% 21 | 0 | 10 |
| 0.05% 21 | 0.3% | 15 |
| 0.05% 21 | 0.6% | 15 |
| 0.03% 22 | 0 | 3 |

TABLE 13-continued

| Compound | Concentration of compound 5 | Length of the figure formed, in mm |
|---|---|---|
| 0.03% 22 | 0.3% | 8 |
| 0.03% 22 | 0.6% | 11 |

EXAMPLE 63

The same formulations as in Example 59 are used, and portions of this composition are mixed with 0.4%, based on the total quantity of the formulation, of the compound 5 and 0.3% of a dye. All operations are carried out under red light. The samples are placed in black plastic lids with a diameter of about 1.5 cm and a height of about 12 mm and are covered wtih a Mylar film. These samples are exposed using daylight and a dose of 1200 mJ/cm². Following exposure, the uncured formulation is poured out and the cured film which remains is developed in ethanol in an ultrasound bath at 23° C. for 1 minute. Drying takes place at 40° C. in a convection oven for 5 minutes. For evaluation, the thickness of the cured layer is measured, which is a measure of the capacity for through-curing. The dyes used and results obtained are reproduced in Table 14:

TABLE 14

| Dye | Thickness of the cured film, in mm |
|---|---|
| Safranin O | 0.56 |
| Methylene blue | 1.15 |

EXAMPLE 64

The procedure of Example 63 is repeated but using, instead of mixtures of borates and dyes, 0.4% of the novel dye-borate salts and a dose of only 200 mJ/cm². The results are reproduced in Table 15:

TABLE 15

| Compound | Thickness of the cured film, in µm |
|---|---|
| 20 | 395 |
| 21 | 48 |
| 22 | 135 |

EXAMPLE 65

The procedure of Example 46 is repeated but adding in each case 1.7% of a free-radical photoinitiator together with 0.4% of the compound 5 and 0.3% of Quantacure ITX. For exposure, however, an iron-doped mercury lamp is used for 40 seconds at a distance of 30 cm. The results are described in Table 16.

TABLE 16

| Free-radical photoinitiator | Number of steps cured |
|---|---|
| Benzil dimethyl ketal | 16 |
| 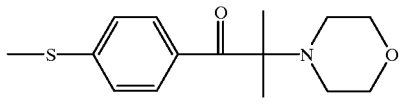 | 13 |
| 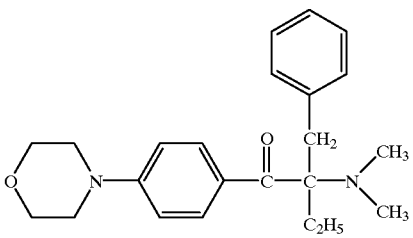 | 8 |
| | 13 |
| 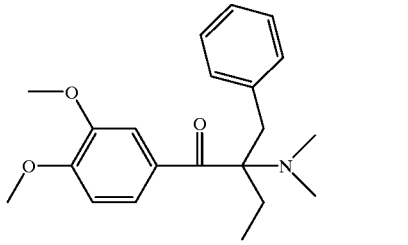 | 13 |

EXAMPLE 66

The procedure of Example 46 is repeated but adding in each case 0.1% of a cationic photoinitiator together with 0.4% of compound 5. The results are described in Table 17.

TABLE 17

| Cationic photoinitiator | Number of steps cured |
|---|---|
| Diphenyliodonium hexafluorophosphate | 6 |
| [Ph-I+-C6H4-O-C8H17 structure with SbF6−] | 6 |
| [Ph-I+-C6H4-O-CH2-CH(OH)-C10H21 structure with SbF6−] | 8 |
| [Bis-triarylsulfonium hexafluorophosphate structure] | 7 |
| [UVI 6990 polymeric triarylsulfonium hexafluorophosphate structure] | |

EXAMPLE 67

The procedure of Example 46 is repeated but adding in each case 0.4% of a cationic photoinitiator together with 0.4% of the compound 5 and 0.3% of a dye. The results are described in Table 18.

TABLE 18
| cationic photoinitiator | dye | Number of steps cured |
|---|---|---|
| Diphenyliodonium hexafluorophosphat | 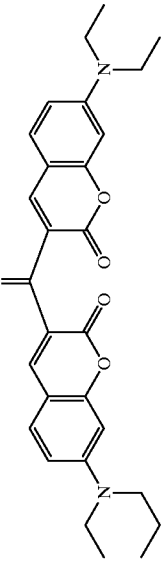 | 16 |
| Diphenyliodonium hexafluorophosphat | 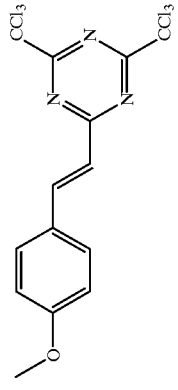 | 13 |
| | 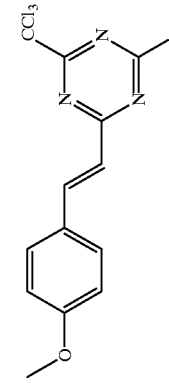 | 13 |
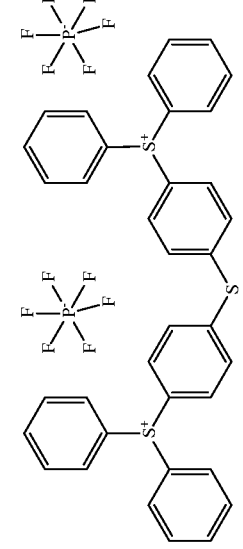
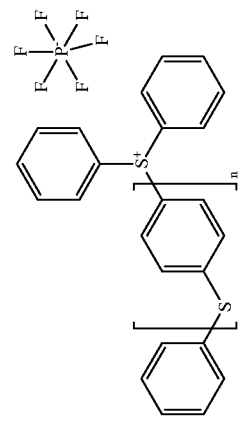 UVI 6990

EXAMPLE 68

0.45% of compound 5 and 0.3% of a dye are mixed in with 20 g of Palatal P 5-01 (BASF). The samples are placed in black plastic lids with a diameter of about 1.5 cm and a height of about 12 mm, and are covered with a Mylar film. These samples are exposed using fluorescent lamps (Philips TL03 40 W) at a distance of 10 cm for 6 minutes. Following exposure, the uncured formulation is poured out and the cured film which remains is dried. For evaluation, a measurement is made of the thickness of the cured film, which is a measurement of the capacity for through-curing. The dyes used and results obtained are reproduced in Table 19.

TABLE 19

| Dye | Thickness of the cured film, in mm |
|---|---|
| Bengal Rose (structure shown) | 10.37 |

EXAMPLE 69

The procedure of example 59 is repeated but 0.4% of the compound 5 and 0,3% of an electron aceptor and 0,3% of a dye are added. The irradiation is carried out for 20 sec with a xenon lamp in a distance of 30 cm. The results are listed in table 20.

TABLE 20

| Elektron aceptor | dye | number of cured steps |
|---|---|---|
| Quantacure ITX | Safranine O | 10 |

EXAMPLE 70

The procedure of example 69 is repeated but 0,3% of the dye-borate salt compounds according to the invention and 0,3% of a dye are added. The results are collected in table 21.

TABLE 21

| Compound | dye or electron aceptorr | number of cured steps |
|---|---|---|
| 22 | 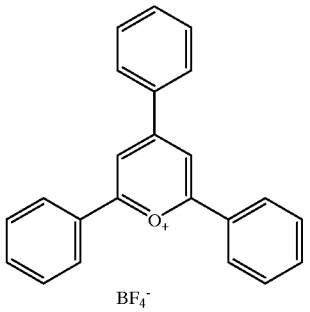 | 12 |

TABLE 21-continued

| Compound | dye or electron aceptorr | number of cured steps |
|---|---|---|
| 20 | 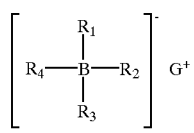 BF$_4^-$ | 7 |

What is claimed is:

1. A compound of formula I $$\left[ R_4 \begin{array}{c} R_1 \\ | \\ -B- \\ | \\ R_3 \end{array} R_2 \right]^- G^+ \quad (I)$$

in which

R$_1$ is C$_1$–C$_{20}$alkyl, C$_3$–C$_{12}$cycloalkyl, C$_2$–C$_8$alkenyl, phenyl-C$_1$–C$_6$alkyl or naphthyl-C$_1$–C$_3$alkyl, where the radicals C$_1$–C$_{20}$alkyl, C$_3$–C$_{12}$cycloalkyl, C$_2$–C$_8$alkenyl, phenyl-C$_1$–C$_6$alkyl or naphthyl-C$_1$–C$_3$alkyl are unsubstituted or are substituted by C$_1$–C$_{12}$alkyl, OR$_6$, R$_7$S(O)$_p$, R$_7$S(O)$_2$O, NR$_8$R$_9$, SiR$_{10}$R$_{11}$R$_{12}$, BR$_{13}$R$_{14}$ or R$_{15}$R$_{16}$P(O)$_q$;

R$_2$, R$_3$ and R$_4$ independently of one another are phenyl or biphenyl, where the radicals phenyl or biphenyl are unsubstituted or are substituted by C$_1$–C$_{12}$alkyl, OR$_6$-substituted-C$_1$–C$_{12}$alkyl, NR$_8$R$_9$-substituted-C$_1$–C$_{12}$alkyl or halogen-substituted C$_1$–C$_{12}$alkyl; or by OR$_6$, R$_7$S(O)$_p$, R$_7$S(O)$_2$O, R$_8$R$_9$NS(O)$_2$, NR$_8$R$_9$, NR$_8$R$_9$CO,

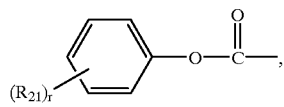

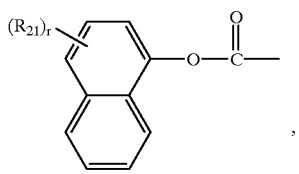

SiR$_{10}$R$_{11}$R$_{12}$, BR$_{13}$R$_{14}$, halogen, or R$_{15}$R$_{16}$P(O)$_q$;
and wherein R$_2$, R$_3$ and R$_4$ are not p-halogenophenyl;

R$_6$ and R$_7$ are C$_1$–C$_{12}$alkyl, halogen-substituted-C$_1$–C$_{12}$alkyl, phenyl-C$_1$–C$_6$alkyl which is unsubstituted or is substituted one to five times by C$_1$–C$_6$alkyl, C$_1$–C$_{12}$alkoxy or halogen; or phenyl which is unsubstituted or is substituted one to five times by C$_1$–C$_6$alkyl, C$_1$–C$_{12}$alkoxy or halogen;

R$_8$, R$_9$, R$_{10}$, R$_{11}$, R$_{12}$, R$_{13}$, R$_{14}$, R$_{15}$ and R$_{16}$ independently of one another are C$_1$–C$_{12}$alkyl, C$_3$–C$_{12}$cycloalkyl, phenyl-C$_1$–C$_6$alkyl which is unsubstituted or is substituted one to five times by C$_1$–C$_6$alkyl, C$_1$–C$_{12}$alkoxy or halogen, or phenyl which is unsubstituted or is substituted one to five times by C$_1$–C$_6$alkyl, C$_1$–C$_{12}$alkoxy or halogen;

p is a number from 0 to 2;

r is a number from 0 to 5;

R$_{21}$ is hydrogen or C$_1$–C$_{12}$alkyl;

q is 0 or 1; and

G is a positive ion; and with the proviso that R$_2$, R$_3$ and R$_4$ are not simultaneously phenyl, pentafluorophenyl, methoxyphenyl or C$_1$–C$_{12}$alkylphenyl.

2. A compound according to claim 1 wherein

R$_2$, R$_3$ and R$_4$ independently of one another are phenyl or biphenyl, where the radicals phenyl or biphenyl are substituted by

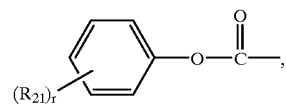

or

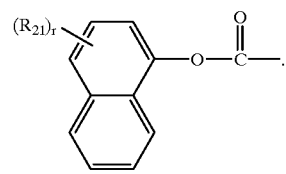

3. A compound of the formula I according to claim 1, in which R$_1$ is C$_1$–C$_{20}$alkyl, C$_3$–C$_{12}$-cycloalkyl, C$_2$–C$_8$alkenyl, phenyl-C$_1$–C$_6$alkyl or naphthyl-C$_1$–C$_3$alkyl, which radicals are unsubstituted or are substitued by C$_1$–C$_{12}$alkyl.

4. A compound of the formula I according to claim 1, in which R$_1$ is C$_1$–C$_{12}$alkyl, allyl, cyclopentyl, cyclohexyl, benzyl or naphthylmethyl.

5. A compound of the formula I according to claim 1, in which R$_2$, R$_3$ and R$_4$ independently of one another are phenyl or biphenyl, which radicals are unsubstituted or are substituted by unsubstituted or $C_1$–$C_6$alkyl or $OR_6$-substituted, $NR_8R_9$-substituted or fluorine-substituted $C_1$–$C_6$alkyl or by $OR_6$, $NR_8R_9$, $BR_{13}R_{14}$, $R_7S(O)_p$ or $R_7S(O)_2O$.

6. A compound of the formula I according to claim 1, in which $R_2$, $R_3$ and $R_4$ independently of one another are phenyl or biphenyl, which radicals are unsubstituted or are substituted by $C_1$–$C_{12}$alkyl, trifluoromethyl, $OR_6$, $NR_8R_9$, halogen, $BR_{13}R_{14}$, $R_7S(O)_p$ or $R_7S(O)_2O$;

$R_6$ is $C_1$–$C_{12}$alkyl, trifluoromethyl, or phenyl which is substituted by $C_1$–$C_6$alkyl, $C_1$–$C_{12}$-alkoxy or halogen;

$R_7$ is $C_4$–$C_{12}$tert-alkyl, trifluoromethyl, or phenyl which is substituted by $C_1$–$C_6$alkyl, $C_1$–$C_{12}$alkoxy or halogen;

$R_8$ and $R_9$ are $C_1$–$C_{12}$alkyl, phenyl or phenyl-$C_1$–$C_6$alkyl;

$R_{13}$ and $R_{14}$ are phenyl which is substituted one to five times by $C_1$–$C_6$alkyl, $C_1$–$C_{12}$alkoxy or halogen.

7. A compound of the formula I according to claim 1, in which $R_2$, $R_3$ and $R_4$ in the formula I are identical.

8. A compound of the formula I according to claim 1, in which G is a dye cation or metal complex cation, a sulfonium, sulfoxonium or iodonium cation, or G is a UV absorber compound which is able to form cations, or G is a metal cation from group I of the Periodic Table, or G is a cation $MY^+$ in which M is a metal from group II of the Periodic Table and Y is alkoxy or halogen, or G is an ammonium salt or phosphonium salt.

9. A compound of the formula I according to claim 1, in which $R_1$ is $C_1$–$C_6$alkyl, $R_2$, $R_3$ and $R_4$ are identical and are phenyl which is substituted by phenoxy, $R_8R_9NS(O)_2$, $NR_8R_9CO$,

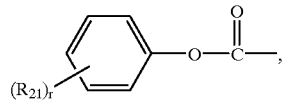

fluorine, bromine, chlorine or halogen-substituted $C_1$–$C_4$alkyl or $R_8$ and $R_9$ are $C_1$–$C_4$alkyl; $R_{21}$ is $C_1$–$C_4$alkyl; r is the number 3; and G is ammonium, trimethylammonium, tetramethylammonium, tetrabutylammonium, tetradecylammonium, trimethyl-n-cetylammonium, cetylpyridinium, methyl-2-chloropyridinium, trimethylhydroxymethylammonium, triethyl-3-bromopropylammonium, triphenylsulfonium, diphenyliodonium, cyanine cation, methylene blue cation, safranin O cation, 3,4-dimethyl-2-(2-hydroxy-3-trimethylamino-propoxy)thioxanthone cation, $(CH_3)_3N^+(CH_2)_6N^+(CH_3)_3$,

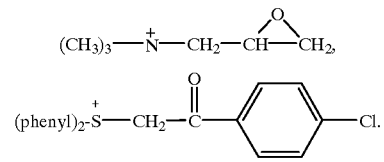

$(phenyl)_3P=N^+=P(phenyl)_3$,

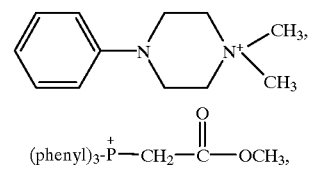

$(phenyl)_3—P^+—CH_2—CH=CH_2$

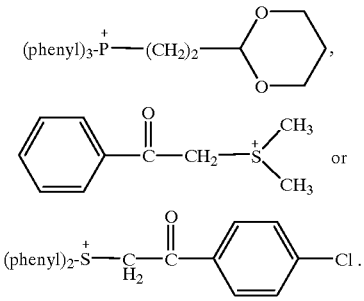

or

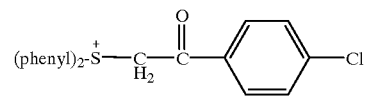

* * * * *